(12) United States Patent
Chang et al.

(10) Patent No.: US 10,870,848 B2
(45) Date of Patent: Dec. 22, 2020

(54) METHODS FOR PREPARING A NEXT GENERATION SEQUENCING (NGS) LIBRARY FROM A RIBONUCLEIC ACID (RNA) SAMPLE AND COMPOSITIONS FOR PRACTICING THE SAME

(71) Applicant: Takara Bio USA, Inc., Mountain View, CA (US)

(72) Inventors: Cynthia Chang, San Mateo, CA (US); Magnolia Bostick, San Mateo, CA (US)

(73) Assignee: Takara Bio USA, Inc., Mountain View, CA (US)

( * ) Notice: Subject to any disclaimer, the term of this patent is extended or adjusted under 35 U.S.C. 154(b) by 26 days.

(21) Appl. No.: 15/746,781

(22) PCT Filed: Sep. 15, 2016

(86) PCT No.: PCT/US2016/051989
§ 371 (c)(1),
(2) Date: Jan. 22, 2018

(87) PCT Pub. No.: WO2017/048993
PCT Pub. Date: Mar. 23, 2017

(65) Prior Publication Data
US 2019/0010489 A1    Jan. 10, 2019

Related U.S. Application Data

(60) Provisional application No. 62/275,957, filed on Jan. 7, 2016, provisional application No. 62/219,084, filed on Sep. 15, 2015.

(51) Int. Cl.
*C12N 15/10* (2006.01)
*C12Q 1/6806* (2018.01)
*C40B 40/08* (2006.01)

(52) U.S. Cl.
CPC ..... *C12N 15/1096* (2013.01); *C12N 15/1093* (2013.01); *C12Q 1/6806* (2013.01); *C40B 40/08* (2013.01)

(58) Field of Classification Search
CPC ............ C12N 15/1096; C12N 15/1093; C12Q 1/6806; C40B 40/08
See application file for complete search history.

(56) References Cited

U.S. PATENT DOCUMENTS

| | | | |
|---|---|---|---|
| 5,962,271 A | 10/1999 | Chenchik et al. | |
| 9,040,256 B2 | 5/2015 | Grunenwald et al. | |
| 9,080,211 B2 | 7/2015 | Grunenwald et al. | |
| 9,085,801 B2 | 7/2015 | Grunenwald et al. | |
| 9,115,396 B2 | 8/2015 | Grunenwald et al. | |
| 2015/0111789 A1 | 4/2015 | Betts et al. | |

FOREIGN PATENT DOCUMENTS

WO    WO2015168161 A2    11/2015

OTHER PUBLICATIONS

Islam et al. (Nature Methods, Feb. 2014, v. 11, No. 2, pp. "163-166", Online Methods, and Supplemental Figures, Notes and Table (pp. 1-25)).*
Islam et al. (Nat. Protoc. 7, 813-828 (2012)).*
Adey, et al. "Ultra-low-input, tagmentation-based whole-genome bisulfite sequencing", Genome Res. 2012. 22: 1139-1143.
Islam, et al. "Characterization of the single-cell transcriptional landscape by highly multiplex RNA-seq", Genome Res. Jul. 2011; 21(7): 1160-1167.
Hashimshony, et al. "CEL-Seq: Single-Cell RNA-Seq by Multiplexed Linear Amplification", Cell Reports 2, 666-673, Sep. 27, 2012.
Jaitin, et al. "Massively parallel single cell RNA-Seq for marker-free decomposition of tissues into cell types", Science. Feb. 14, 2014; 343(6172): 776-779.
Wang, et al. "Tagmentation-based whole-genome bisulfite sequencing", Nature Protocol 8(10):2022-32—Oct. 2013.
Islam, et al. "Quantitative single-cell RNA-seq with unique molecular identifiers", Nature Methods, vol. 11, No. 2, Feb. 1, 2014 (Feb. 1, 2014 ), pp. 163-166.
Islam, et al. "Highly multiplexed and strand-specific single-cell RNA 5' end sequencing", Nature Protocols vol. 7, pp. 813-828 (2012).
Picelli, et al. "Full-length RNA-seq from single cells using Smart-seq2", Nature Protocols, vol. 9, No. 1, Jan. 1, 2014 (Jan. 1, 2014).
Saliba, et al., "Single-cell RNA-seq: advances and future challenges", Nucleic Acids Research, vol. 42, No. 14, Jul. 22, 2014 (Jul. 22, 2014), pp. 8845-8860.

* cited by examiner

*Primary Examiner* — Robert H Havlin
(74) *Attorney, Agent, or Firm* — Bret E. Field; Bozicevic, Field & Francis LLP

(57) ABSTRACT

Methods of preparing a next generation sequencing (NGS) library from a ribonucleic acid (RNA) sample are provided. Aspects of the methods include combining the RNA sample with a first strand cDNA primer and a template switch oligo-nucleotide under first strand cDNA synthesis conditions, where one of the first strand cDNA primer and the template switch oligo-nucleotide includes a first post-tagmentation amplification primer binding domain. The resultant product is subjected to amplification conditions sufficient to produce a double stranded cDNA, which is then tagmented with a transposome that includes a second post-tagmentation amplification primer binding domain. The tagmented sample is then subjected to amplification conditions using first and second post-tagmentation amplification primers that include sequencing platform adapter constructs to produce a NGS library. Aspects of the invention further include compositions produced by the methods and kits that find use in practicing the methods.

23 Claims, 15 Drawing Sheets
Specification includes a Sequence Listing.

cDNA

| Size [bp] | Conc. [pg/μl] | Molarity [pmol/l] | Yield [ng] |
|---|---|---|---|
| 1,881 | 1,497.69 | 1,206.50 | 18.0 |

Library

| Size [bp] | Conc. [pg/μl] | Molarity [pmol/l] | Yield [ng] |
|---|---|---|---|
| 419 | 8,694.52 | 31,434.80 | 130.4 |

AAGCAGTGGTATCAACGCAGAGTACGTGTGCTCTTCCGATCTCTTGTANNNNNT(30)VN
　　　　　　　　II A　　　　　　　　　　　RP2　　　　　　In-line　(UMI)
　　　(For cDNA amplification)　　(For library amplification)　Index 12

METHODS FOR PREPARING A NEXT GENERATION SEQUENCING (NGS) LIBRARY FROM A RIBONUCLEIC ACID (RNA) SAMPLE AND COMPOSITIONS FOR PRACTICING THE SAME

CROSS-REFERENCE TO RELATED APPLICATIONS

This application is related to U.S. Provisional Patent Application Ser. No. 62/219,084 filed Sep. 15, 2015 and U.S. Provisional Patent Application Ser. No. 62/275,957 filed Jan. 7, 2016; the disclosures of which applications are herein incorporated by reference.

INTRODUCTION

Massively parallel (or "next generation") sequencing platforms are rapidly transforming data collection and analysis in genome, epigenome and transcriptome research. Certain sequencing platforms, such as those marketed by Illumina®, Ion Torrent™, Roche™, and Life Technologies™, involve solid phase amplification of target polynucleotides of unknown sequence. Solid phase amplification of these polynucleotides is typically performed by first ligating known adapter sequences to each end of a target polynucleotide. The double-stranded polynucleotide is then denatured to form a single-stranded template molecule that is immobilized on the solid substrate. The adapter sequence on the 3' end of the template is hybridized to an extension primer, and amplification is performed by extending the primer.

A disadvantage of ligation-based approaches for sequencing adapter addition is the number of steps involved, including the enzymatic and wash steps that are needed to prepare the target polynucleotide before amplification can be initiated. As one example, after ligation of the adapter sequences, unused adapter molecules must be separated from the ligated polynucleotides before proceeding to the amplification, so as to avoid unwanted amplification of adapters that have not been attached to the target polynucleotides. The unused adapter molecules may also hybridize to the amplification primers, preventing efficient hybridization of the primers to the template molecules and subsequent extension.

An additional drawback of ligation-based approaches is their lack of directionality, which makes it difficult to have different adapters at the different ends of the nucleic acids. Moreover, the sensitivity of such methods is low and renders them unsuitable under circumstances where only a small amount of sample material is available.

SUMMARY

Methods of preparing a next generation sequencing (NGS) library from a ribonucleic acid (RNA) sample are provided. Aspects of the methods include combining the RNA sample with a first strand cDNA primer and a template switch oligonucleotide under first strand cDNA synthesis conditions, where one of the first strand cDNA primer and the template switch oligonucleotide includes a first post-tagmentation amplification, e.g., PCR amplification, primer binding domain. The resultant product is subjected to amplification conditions sufficient to produce a double stranded cDNA, which product is then tagmented with a transposome that includes a second post-tagmentation amplification, e.g., PCR amplification, primer binding domain. The tagmented sample is then subjected to amplification conditions, such as PCR amplification conditions, using first and second amplification primers that include sequencing platform adapter constructs to produce a NGS library. Aspects of the invention further include compositions produced by the methods and kits that find use in practicing the methods.

BRIEF DESCRIPTION OF THE FIGURES

FIGS. 10A to 10D show results of various aspects of a single transposome mediated NGS library production protocol (illustrated in FIG. 3D) from single cells.

DEFINITIONS

Figure 1:
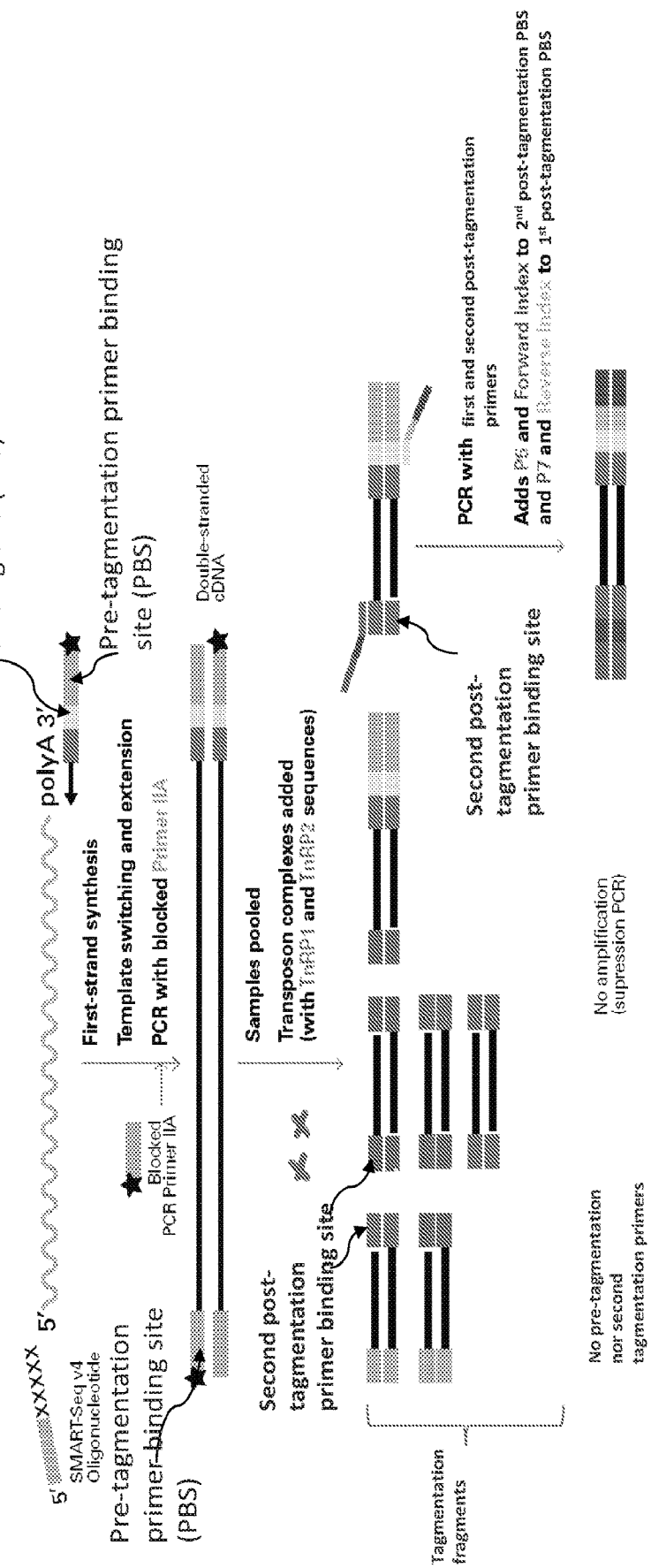
FIG. 1 schematically illustrates an embodiment of the methods of the disclosure.

A domain refers to a stretch or length of a nucleic acid made up of a plurality of nucleotides, where the stretch or length provides a defined function to the nucleic acid. Examples of domains include primer binding domains, hybridization domains, barcode domains (such as source barcode domains), unique molecular identifier domains, NGS adaptor domains, NGS indexing domains, etc. While the length of a given domain may vary, in some instances the length ranges from 2 to 100 nt, such as 5 to 50 n, e.g., 5 to 30 nt.

Amplification primer binding domains are domains that are configured to bind via hybridization to an amplification primer. Pre-tagmentation amplification primer binding domains are domains which are configured to bind to pre-tagmentation amplification primers during an amplification that occurs before a tagmentation step, e.g., a cDNA amplification protocol which occurs prior to a tagemention step. Post-tagmentation amplification primer binding domains are domains which are configured to bind to post-tagmentation amplification primers during an amplification that occurs after a tagmentation step, e.g., a tagmented sample amplification protocol which occurs after to a tagmentation step.

A barcode domain is a domain that serves as an identifier of a nucleic acid. Barcode domains may vary, wherein examples include RNA source barcode domains, e.g., cell barcode domains, host barcode domains, etc.; container barcode domains, such as plate or well barcode domains; in-line barcode domains, indexing barcode domains, etc.

Unique Molecular Identifiers are employed in many next generation sequencing applications. Unique Molecular Identifiers (i.e., UMIs) are randomers of varying length, e.g., ranging in length in some instances from 6 to 12 nts, that can be used for counting of individual molecules of a given molecular species. Counting is achieved by attaching UMIs from a diverse pool of UMIs to individual molecules of a target of interest such that each individual molecule receives a unique UMI. By counting individual transcript molecules, PCR bias can be reduced during NGS library prep and a more quantitative understanding of the sample population can be achieved. See e.g., U.S. Pat. No. 8,835,358; Fu et al., "Molecular Indexing Enables Quantitative Targeted RNA Sequencing and Reveals Poor Efficiencies in Standard Library Preparations," PNAS (2014) 5: 1891-1896 and Fu et al., "Digital Encoding of Cellular mRNAs Enabling Precise and Absolute Gene Expression Measurement by Single-Molecule Counting," Anal. Chem (2014) 86:2867-2870.

The term "complementary" as used herein refers to a nucleotide sequence that base-pairs by non-covalent bonds to all or a region of a target nucleic acid (e.g., a template RNA or other region of the double stranded product nucleic acid). In the canonical Watson-Crick base pairing, adenine (A) forms a base pair with thymine (T), as does guanine (G) with cytosine (C) in DNA. In RNA, thymine is replaced by uracil (U). As such, A is complementary to T and G is complementary to C. In RNA, A is complementary to U and vice versa. Typically, "complementary" refers to a nucleotide sequence that is at least partially complementary. The term "complementary" may also encompass duplexes that are fully complementary such that every nucleotide in one strand is complementary to every nucleotide in the other strand in corresponding positions. In certain cases, a nucleotide sequence may be partially complementary to a target, in which not all nucleotides are complementary to every nucleotide in the target nucleic acid in all the corresponding positions. For example, a primer may be perfectly (i.e., 100%) complementary to the target nucleic acid, or the primer and the target nucleic acid may share some degree of complementarity which is less than perfect (e.g., 70%, 75%, 85%, 90%, 95%, 99%). The percent identity of two nucleotide sequences can be determined by aligning the sequences for optimal comparison purposes (e.g., gaps can be introduced in the sequence of a first sequence for optimal alignment). The nucleotides at corresponding positions are then compared, and the percent identity between the two sequences is a function of the number of identical positions shared by the sequences (i.e., % identity=# of identical positions/total# of positions×100). When a position in one sequence is occupied by the same nucleotide as the corresponding position in the other sequence, then the molecules are identical at that position. A non-limiting example of such a mathematical algorithm is described in Karlin et al., Proc. Natl. Acad. Sci. USA 90:5873-5877 (1993). Such an algorithm is incorporated into the NBLAST and XBLAST programs (version 2.0) as described in Altschul et al., Nucleic Acids Res. 25:389-3402 (1997). When utilizing BLAST and Gapped BLAST programs, the default parameters of the respective programs (e.g., NBLAST) can be used. In one aspect, parameters for sequence comparison can be set at score=100, wordlength=12, or can be varied (e.g., wordlength=5 or wordlength=20).

As used herein, the term "hybridization conditions" means conditions in which a primer specifically hybridizes to a region of the target nucleic acid (e.g., a template RNA or other region of the double stranded product nucleic acid). Whether a primer specifically hybridizes to a target nucleic acid is determined by such factors as the degree of complementarity between the polymer and the target nucleic acid and the temperature at which the hybridization occurs, which may be informed by the melting temperature ($T_M$) of the primer. The melting temperature refers to the temperature at which half of the primer-target nucleic acid duplexes remain hybridized and half of the duplexes dissociate into single strands. The $T_m$ of a duplex may be experimentally determined or predicted using the following formula $T_m=81.5+16.6(\log_{10} [Na^+])+0.41$ (fraction G+C)−(60/N), where N is the chain length and [$Na^+$] is less than 1 M. See Sambrook and Russell (2001; Molecular Cloning: A Laboratory Manual, $3^{rd}$ ed., Cold Spring Harbor Press, Cold Spring Harbor N.Y., Ch. 10). Other more advanced models that depend on various parameters may also be used to predict $T_m$ of primer/target duplexes depending on various hybridization conditions. Approaches for achieving specific nucleic acid hybridization may be found in, e.g., Tijssen, Laboratory Techniques in Biochemistry and Molecular Biology-Hybridization with Nucleic Acid Probes, part I, chapter 2, "Overview of principles of hybridization and the strategy of nucleic acid probe assays," Elsevier (1993).

DETAILED DESCRIPTION

Methods of preparing a next generation sequencing (NGS) library from a ribonucleic acid (RNA) sample are provided. Aspects of the methods include combining the RNA sample with a first strand cDNA primer and a template switch oligonucleotide under first strand cDNA synthesis conditions. In some instances, the first strand cDNA primer includes two amplification binding sites, one for pre-tagmentation amplification (e.g., cDNA amplification) and one for post-tagmentation amplification, such as library amplification (e.g., first post-tagmentation amplification site) and the template switch oligonucleotide includes a complementary pre-tagmentation amplification e.g., PCR amplification, primer binding domain. The resultant product is subjected to amplification, e.g., PCR amplification, with a single primer complementary to the pre-tagmentation amplification binding site found on both the first strand cDNA synthesis primer and the template switch oligonucleotide under conditions sufficient to produce a double stranded cDNA. The resultant product is then tagmented with a transposome that includes a second post-tagmentation amplification primer binding domain. The tagmented sample is then subjected to amplification conditions using two primers that complement the first and second post-tagmentation amplification sites introduced in the cDNA by synthesis and tagmentation, respectively, to produce a NGS library. Aspects of the invention further include compositions produced by the methods and kits that find use in practicing the methods.

Before the methods of the present disclosure are described in greater detail, it is to be understood that the methods are not limited to particular embodiments described, as such may, of course, vary. It is also to be understood that the terminology used herein is for the purpose of describing particular embodiments only, and is not intended to be limiting, since the scope of the methods will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the methods. The upper and lower limits of these smaller ranges may independently be included in the smaller ranges and are also encompassed within the methods, subject to any specifically excluded limit in the stated range. Where the stated range includes one or both of the limits, ranges excluding either or both of those included limits are also included in the methods.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which the methods belong. Although any methods similar or equivalent to those described herein can also be used in the practice or testing of the methods, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present methods are not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the methods, which are, for clarity, described in the context of separate embodiments, may also be provided in combination in a single embodiment. Conversely, various features of the methods, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed, to the extent that such combinations embrace operable processes and/or devices/systems/kits. In addition, all sub-combinations listed in the embodiments describing such variables are also specifically embraced by the present methods and are disclosed herein just as if each and every such sub-combination was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present methods. Any recited method can be carried out in the order of events recited or in any other order which is logically possible.

General Overview

As summarized above, the invention provides methods of preparing a next generation sequencing (NGS) library from a ribonucleic acid (RNA) sample. NGS libraries produced by methods of the invention are those whose nucleic acid members include a partial or complete sequencing platform adapter sequence at their termini useful for sequencing using a sequencing platform of interest. Sequencing platforms of interest include, but are not limited to, the HiSeq™, MiSeq™ and Genome Analyzer™ sequencing systems from Illumina®; the Ion PGM™ and Ion Proton™ sequencing systems from Ion Torrent™; the PACBIO RS II Sequel system from Pacific Biosciences, the SOLiD sequencing systems from Life Technologies™, the 454 GS FLX+ and GS Junior sequencing systems from Roche, the MinION™ system from Oxford Nanopore, or any other sequencing platform of interest.

In some embodiments, the methods of the disclosure can be performed according to the schematic diagrammed in FIG. 1. As illustrated in FIG. 1, an RNA target (squiggly (blue) line) can be contacted with a first primer (e.g., a cDNA synthesis primer) that includes a pre-tagmentation amplification primer binding domain (i.e., pre-tagmentation amplification primer binding site (PBS) (indicated in green with a star at terminus) and a first post-tagmentation primer binding domain domain (i.e., first post-tagmentation amplification PBS (indicated in yellow) and an RNA binding domain or site (e.g., oligo dT, (indicated in pink)). First strand synthesis and template switching is performed as illustrated, e.g., using the SMART-Seq v4 template switch oligonucleotide (Takara Bio USA, Inc, Mountain View Calif.) (indicated by a 5' green domain and a 3' XXXXX domain). In some embodiments, the template switch oligonucleotide includes a pre-tagmentation amplification primer binding domain (i.e., pre-tagmentation amplification PBS). The pre-tagmentation amplification PBS can be the same as the pre-tagmentation amplification PBS on the cDNA synthesis primer. In some instances, the template switch oligonucleotide can include a first post-tagmentation amplification PBS or any additional sequence (e.g., as described below). The cDNA resulting from template switching can be amplified with a primer (e.g., blocked PCR primer IIA) that binds to the pre-tagmentation amplification primer binding domains (i.e., pre-tagmentation primer binding sites) at both ends of the cDNA, thereby generating a double-stranded cDNA. The double-stranded cDNA can be contacted with transposon complexes that include one or more second post-tagmentation amplification primer binding domains (i.e., post-tagmentation amplification primer binding sites, e.g., TnRP1 and/or TnRP2). The second post-tagmentation amplification primer binding domains can be randomly attached to fragment ends of the double-stranded cDNA library according to tagmentation and transposon mechanisms of action. The resulting tagmentation fragments are diagrammed in FIG. 1. The fragments can be amplified with a primer that binds to the second post-tagmentation amplification primer binding domain (e.g., orange box) and a primer that binds to the first post-tagmentation amplification primer binding domain (e.g., yellow box). These two primers can include additional sequencing adaptor sequences, such as the P5 and P7 sequences, as well as the forward and reverse indexes (e.g., i5, i7) for sequencing, as desired.

The use of the first and second post-tagmentation amplification primers allows for selective amplification of an end (e.g., 3' end) fragment. Other fragments are not amplified either because the correct primers are missing, or due to suppression effects during PCR.

Methods

Aspects of the methods include combining an RNA sample, e.g., a mRNA sample, with a first strand cDNA synthesis primer (i.e., a first strand CDS primer), a template switch oligonucleotide (i.e., a TSO), a reverse transcriptase, and dNTPs, in a reaction mixture under first strand cDNA synthesis conditions, e.g., conditions sufficient to produce a double stranded product nucleic acid that includes the template RNA and the template switch oligonucleotide each hybridized to adjacent regions of a first strand complementary deoxyribonucleic acid (cDNA), where the first strand cDNA includes the first strand cDNA synthesis primer at its 5' end and a newly synthesized length or portion that is complementary to domains found in the template RNA and template switch oligonucleotide, wherein this newly synthesized domain is covalently bonded to the 3' end of the first strand cDNA synthesis primer. In certain aspects, one of the first strand cDNA primer and the template switch oligonucleotide includes a pre-tagmentation amplification primer binding domain for cDNA amplification, e.g., PCR amplification, with a single primer complementary to at least a sequence or site of the pre-tagmentation primer binding domain.

By "conditions sufficient to produce a double stranded product nucleic acid" is meant reaction conditions that permit polymerase-mediated extension of a 3' end of the first strand cDNA primer hybridized to the template RNA, template switching of the polymerase to the template switch oligonucleotide, and continuation of the extension reaction using the template switch oligonucleotide as the template. Achieving suitable reaction conditions may include selecting reaction mixture components, concentrations thereof, and a reaction temperature to create an environment in which the polymerase is active and the relevant nucleic acids in the reaction interact (e.g., hybridize) with one another in the desired manner. For example, in addition to the template RNA, the polymerase, the first strand cDNA primer, the template switch oligonucleotide and dNTPs, the reaction mixture may include buffer components that establish an appropriate pH, salt concentration (e.g., KCl concentration), metal cofactor concentration (e.g., $Mg^{2+}$ or $Mn^{2+}$ concentration), and the like, for the extension reaction and template switching to occur. Other components may be included, such as one or more nuclease inhibitors (e.g., an RNase inhibitor and/or a DNase inhibitor), one or more additives for facilitating amplification/replication of GC rich sequences (e.g., GC-Melt™ reagent (Takara Bio USA, Inc. (Mountain View, Calif.)), betaine, DMSO, ethylene glycol, 1,2-propanediol, or combinations thereof), one or more molecular crowding agents (e.g., polyethylene glycol, Ficoll, dextran, or the like), one or more enzyme-stabilizing components (e.g., DTT, or TCEP, present at a final concentration ranging from 1 to 10 mM (e.g., 5 mM)), and/or any other reaction mixture components useful for facilitating polymerase-mediated extension reactions and template-switching.

The reaction mixture can have a pH suitable for the primer extension reaction and template-switching. In certain embodiments, the pH of the reaction mixture ranges from 5 to 9, such as from 7 to 9, including from 8 to 9, e.g., 8 to 8.5. In some instances, the reaction mixture includes a pH adjusting agent. pH adjusting agents of interest include, but are not limited to, sodium hydroxide, hydrochloric acid, phosphoric acid buffer solution, citric acid buffer solution, and the like. For example, the pH of the reaction mixture can be adjusted to the desired range by adding an appropriate amount of the pH adjusting agent.

The temperature range suitable for production of the double stranded product nucleic acid may vary according to factors such as the particular polymerase employed, the melting temperatures of any optional primers employed, etc. According to one embodiment, the polymerase is a reverse transcriptase (e.g., an MMLV reverse transcriptase) and the reaction mixture conditions sufficient to produce the double stranded product nucleic acid include bringing the reaction mixture to a temperature ranging from 4° C. to 72° C., such as from 16° C. to 70° C., e.g., 37° C. to 50° C., such as 40° C. to 45° C., including 42° C.

The template ribonucleic acid (RNA) within the RNA sample may be a polymer of any length composed of ribonucleotides, e.g., 10 nts or longer, 20 nts or longer, 50 nts or longer, 100 nts or longer, 500 nts or longer, 1000 nts or longer, 2000 nts or longer, 3000 nts or longer, 4000 nts or longer, 5000 nts or longer or more nts. In certain aspects, the template ribonucleic acid (RNA) is a polymer composed of ribonucleotides, e.g., 10 nts or less, 20 nts or less, 50 nts or less, 100 nts or less, 500 nts or less, 1000 nts or less, 2000 nts or less, 3000 nts or less, 4000 nts or less, or 5000 nts or less, 10,000 nts or less, 25,000 nts or less, 50,000 nts or less, 75,000 nts or less, 100,000 nts or less. The template RNA may be any type of RNA (or sub-type thereof) including, but not limited to, a messenger RNA (mRNA), a microRNA (miRNA), a small interfering RNA (siRNA), a transacting small interfering RNA (ta-siRNA), a natural small interfering RNA (nat-siRNA), a ribosomal RNA (rRNA), a transfer RNA (tRNA), a small nucleolar RNA (snoRNA), a small nuclear RNA (snRNA), a long non-coding RNA (lncRNA), a non-coding RNA (ncRNA), a transfer-messenger RNA (tmRNA), a precursor messenger RNA (pre-mRNA), a small Cajal body-specific RNA (scaRNA), a piwi-interacting RNA (piRNA), an endoribonuclease-prepared siRNA (esiRNA), a small temporal RNA (stRNA), a signal recognition RNA, a telomere RNA, a ribozyme, or any combination of RNA types thereof or subtypes thereof.

The RNA sample that includes the template RNA may be combined into the reaction mixture in an amount sufficient for producing the product nucleic acid. According to one embodiment, the RNA sample is combined into the reaction mixture such that the final concentration of RNA in the reaction mixture is from 1 fg/μL to 10 μg/μL, such as from 1 pg/μL to 5 μg/μL, such as from 0.001 μg/μL to 2.5 μg/μL, such as from 0.005 μg/μL to 1 μg/μL, such as from 0.01 μg/μL to 0.5 μg/μL, including from 0.1 μg/μL to 0.25 μg/μL. In certain aspects, the RNA sample that includes the template RNA is isolated from a single cell. In other aspects, the RNA sample that includes the template RNA is isolated from 2, 3, 4, 5, 6, 7, 8, 9, 10 or more, 20 or more, 50 or more, 100 or more, or 500 or more cells, such as 750 or more cells, 1,000 or more cells, 2,000 or more cells, including 5,000 or more cells. According to certain embodiments, the RNA sample that includes the template RNA is isolated from 500 or less, 100 or less, 50 or less, 20 or less, 10 or less, 9, 8, 7, 6, 5, 4, 3, or 2 cells.

The template RNA may be present in any nucleic acid sample of interest, including but not limited to, a nucleic acid sample isolated from a single cell, a plurality of cells (e.g., cultured cells), a tissue, an organ, or an organism (e.g., bacteria, yeast, or higher eukaryotic organisms, such as a plant, or a mouse, or a worm, or the like). In certain aspects, the nucleic acid sample is isolated from a cell(s), tissue, organ, and/or the like of a mammal (e.g., a human, a rodent (e.g., a mouse), or any other mammal of interest). In other aspects, the sample may be isolated from a bodily compartment suitable for use in diagnosis, such as blood, urine, saliva, platelets, microvesicles, exosomes, serum, or other bodily fluids. In other aspects, the nucleic acid sample is isolated from a source other than a mammal, such as bacteria, yeast, insects (e.g., *Drosophila*), amphibians (e.g., frogs (e.g., *Xenopus*)), viruses, plants, or any other non-mammalian nucleic acid sample source.

Approaches, reagents and kits for isolating RNA from such sources are known in the art. For example, kits for isolating RNA from a source of interest—such as the NucleoSpin®, NucleoMag® and NucleoBond® RNA isolation kits by Clontech Laboratories, Inc. (Mountain View, Calif.)—are commercially available. In certain aspects, the RNA is isolated from a fixed biological sample, e.g., formalin-fixed, paraffin-embedded (FFPE) tissue. RNA from FFPE tissue may be isolated using commercially available kits—such as the NucleoSpin® FFPE RNA kits by Clontech Laboratories, Inc. (Mountain View, Calif.).

In certain aspects, the subject methods include producing the template RNA from a precursor RNA. For example, when it is desirable to control the size of the template RNA that is combined into the reaction mixture, an RNA sample from a source of interest may be subjected to shearing/fragmentation, e.g., to generate a sample that includes template RNAs that are shorter in length as compared to precursor non-sheared RNAs (e.g., full-length mRNAs) in the original sample. In some embodiments, the RNA may be used directly from the lysed cell by placing the cell in a suitable buffer (e.g., a hypotonic solution), optionally in the presence of detergent (e.g. Tween-20, Triton X100, NP40, and/or CHAPs), so as to lyse the cell. RT reaction components may then be added directly to the lysate without further isolation to generate cDNA from the cellular RNA. The template RNA may be generated by a shearing/fragmentation strategy including, but not limited to, passing the sample one or more times through a micropipette tip or fine-gauge needle, nebulizing the sample, sonicating the sample (e.g., using a focused-ultrasonicator by Covaris, Inc. (Woburn, Mass.)), bead-mediated shearing, enzymatic shearing (e.g., using one or more RNA-shearing enzymes, or by enzymatic digestions, e.g., with restriction enzymes or other endonucleases appropriate for the polynucleotides of interest), chemical based fragmentation, e.g., using divalent cations, fragmentation buffer (which may be used in combination with heat) or any other suitable approach for shearing/fragmenting a precursor RNA to generate a shorter template RNA. In certain aspects, the template RNA generated by shearing/fragmentation of a starting nucleic acid sample has a length of from 10 to 20 nts, from 20 to 30 nts, from 30 to 40 nts, from 40 to 50 nts, from 50 to 60 nts, from 60 to 70 nts, from 70 to 80 nts, from 80 to 90 nts, from 90 to 100 nts, from 100 to 150 nts, from 150 to 200 nts, from 200 to 250 nts in length, or from 200 to 1000 nts or even from 1000 to 10,000 nts in length, for example, as appropriate for the sequencing platform chosen.

Additional strategies for producing a template RNA from a precursor RNA may be employed. For example, producing a template RNA may include adding nucleotides to an end of the precursor RNA. In certain aspects, the precursor RNA is a non-polyadenylated RNA (e.g., a microRNA, small RNA, or the like), and producing the template RNA includes adenylating (e.g., polyadenylating) the precursor RNA. Adenylating the precursor RNA may be performed using any convenient approach. According to certain embodiments, the adenylation is performed enzymatically, e.g., using Poly(A) polymerase or any other enzyme suitable for catalyzing the incorporation of adenine residues at the 3' terminus of the precursor RNA. Reaction mixtures for carrying out the adenylation reaction may include any useful components, including but not limited to, a polymerase, a buffer (e.g., a Tris-HCL buffer), one or more metal cations (e.g., $MgCl_2$, $MnCl_2$, or combinations thereof), a salt (e.g., NaCl), one or more enzyme-stabilizing components (e.g., DTT), ATP, and any other reaction components useful for facilitating the adenylation of a precursor RNA. The adenylation reaction may be carried out at a temperature (e.g., 30° C.-50° C., such as 37° C.) and pH (e.g., pH 7-pH 8.5, such as pH 7.9) compatible with the polymerase being employed, e.g., polyA polymerase. Other approaches for adding nucleotides to a precursor RNA include ligation-based strategies, where an RNA ligase (e.g., T4 RNA ligase) catalyzes the covalent joining of a defined sequence to an end (e.g., the 3' end) of the precursor RNA to produce a template RNA.

The methods of the present disclosure include combining a polymerase into the reaction mixture. A variety of polymerases may be employed when practicing the subject methods. The polymerase combined into the reaction mixture is capable of template switching, where the polymerase uses a first nucleic acid strand as a template for polymerization, and then switches to the 3' end of a second "acceptor" template nucleic acid strand to continue the same polymerization reaction (e.g., template switching). In certain aspects, the polymerase combined into the reaction mixture is a reverse transcriptase (RT). Reverse transcriptases capable of template-switching that find use in practicing the methods include, but are not limited to, retroviral reverse transcriptase, retrotransposon reverse transcriptase, retroplasmid reverse transcriptases, retron reverse transcriptases, bacterial reverse transcriptases, group II intron-derived reverse transcriptase, and mutants, variants, derivatives, or functional fragments thereof, e.g., RNase H minus or RNase H reduced enzymes (e.g. Superscript RT (Thermo Fisher)). For example, the reverse transcriptase may be a Moloney Murine Leukemia Virus reverse transcriptase (MMLV RT) or a Bombyx mori reverse transcriptase (e.g., Bombyx mori R2 non-LTR element reverse transcriptase). Polymerases capable of template switching that find use in practicing the subject methods are commercially available and include SMARTScribe™ reverse transcriptase available from Takara Bio USA, Inc. (Mountain View, Calif.). In certain aspects, a mix of two or more different polymerases is added to the reaction mixture, e.g., for improved processivity, proof-reading, and/or the like. In some instances, the polymer is one that is heterologous relative to the template, or source thereof.

The polymerase is combined into the reaction mixture such that the final concentration of the polymerase is sufficient to produce a desired amount of the product nucleic acid. In certain aspects, the polymerase (e.g., a reverse transcriptase such as an MMLV RT or a Bombyx mori RT) is present in the reaction mixture at a final concentration of from 0.1 to 200 units/μL (U/μL), such as from 0.5 to 100 U/μL, such as from 1 to 50 U/μL, including from 5 to 25 U/μL, e.g., 20 U/μL.

In addition to a template switching capability, the polymerase combined into the reaction mixture may include other useful functionalities to facilitate production of the product nucleic acid. For example, the polymerase may have terminal transferase activity, where the polymerase is capable of catalyzing template-independent addition of deoxyribonucleotides to the 3' hydroxyl terminus of a DNA molecule. In certain aspects, when the polymerase reaches the 5' end of a template RNA, the polymerase is capable of incorporating one or more additional nucleotides at the 3' end of the nascent strand not encoded by the template. For example, when the polymerase has terminal transferase activity, the polymerase may be capable of incorporating 1, 2, 3, 4, 5, 6, 7, 8, 9, 10 or more additional nucleotides at the 3' end of the nascent DNA strand. In certain aspects, a polymerase having terminal transferase activity incorporates 10 or less, such as 5 or less (e.g., 3) additional nucleotides at the 3' end of the nascent DNA strand. All of the nucleotides may be the same (e.g., creating a homonucleotide stretch at the 3' end of the nascent strand) or at least one of the nucleotides may be different from the other(s). In certain aspects, the terminal transferase activity of the polymerase results in the addition of a homonucleotide stretch of 2, 3, 4, 5, 6, 7, 8, 9, 10 or more of the same nucleotides (e.g., all dCTP, all dGTP, all dATP, or all dTTP). According to certain embodiments, the terminal transferase activity of the polymerase results in the addition of a homonucleotide stretch of 10 or less, such as 9, 8, 7, 6, 5, 4, 3, or 2 (e.g., 3) of the same nucleotides. For example, according to one embodiment, the polymerase is an MMLV reverse transcriptase (MMLV RT). MMLV RT incorporates additional nucleotides (predominantly dCTP, e.g., three dCTPs) at the 3' end of the nascent DNA strand. As described in greater detail elsewhere herein, these additional nucleotides may be useful for enabling hybridization between the 3' end of the template switch oligonucleotide and the 3' end of the nascent DNA strand, e.g., to facilitate template switching by the polymerase from the template RNA to the template switch oligonucleotide. For example, when a homonucleotide stretch is added to the nascent cDNA strand, the template switch oligonucleotide may have a 3' hybridization domain complementary to the homonucleotide stretch to enable hybridization between the 3' end of the template switch oligonucleotide and the 3' end of the nascent cDNA strand. Similarly, when a heteronucleotide stretch is added to the nascent cDNA strand, the template switch oligonucleotide may have a 3' hybridization domain complementary to the heteronucleotide stretch to enable hybridization between the 3' end of the template switch oligonucleotide and the 3' end of the nascent cDNA strand.

As summarized above, the reaction mixture further includes a first strand cDNA primer. According to certain embodiments, the primer includes two or more domains. For example, the primer may include a first (e.g., 3') domain that hybridizes to the template RNA and a second (e.g., 5') domain that does not hybridize to the template RNA. The sequence of the first and second domains may be independently defined or arbitrary. In certain aspects, the first domain has a defined sequence (e.g., an oligo dT sequence or an RNA specific sequence) or an arbitrary sequence (e.g., a random sequence, such as a random hexamer sequence) and the sequence of the second domain is defined, e.g., an pre-tagmentation amplification primer binding domain, such as PCR primer binding domain (i.e., pre-tagmentation amplification primer binding site). According to one embodiment, the second domain includes a nucleotide sequence that is the same as a nucleotide sequence present in the template switch oligonucleotide, e.g., where the pre-tagmentation amplification primer binding domains are the same and the first and second pre-tagmentation amplification primers share identical. In certain aspects, the second domain includes a nucleotide sequence that is different from a nucleotide sequence present in the template switch oligonucleotide, e.g., where the sequences of the pre-tagmentation amplification primer binding domains are different and bind to amplification primers of corresponding different sequences.

In addition to the first and second domains described above, the first strand cDNA primer may further include a first post-tagmentation amplification, e.g., PCR amplification, primer binding domain. This post-tagmentation amplification primer binding domain may be positioned, e.g., between the first and second domains, and may have any convenient sequence. According to one embodiment, the post-tagmentation amplification primer binding domain includes a NGS read primer domain. In certain aspects, the first strand cDNA primer includes a barcode domain for identification of the sample after pooling post-cDNA amplification. In certain aspects, the first strand cDNA primer may include a unique molecular identifier or other barcode to mark each RNA molecule converted to cDNA individually. In some instances, the sequence includes all or a component of a sequencing platform adapter construct. By "sequencing platform adapter construct" is meant a nucleic acid construct that includes at least a portion of a nucleic acid domain (e.g., a sequencing platform adapter nucleic acid sequence) utilized by a sequencing platform of interest, such as a sequencing platform provided by Illumina® (e.g., the HiSeq™, MiSeq™ and/or Genome Analyzer™ sequencing systems); Ion Torrent™ (e.g., the Ion PGM™ and/or Ion Proton™ sequencing systems); Pacific Biosciences (e.g., the PACBIO RS II sequencing system); Life Technologies™ (e.g., a SOLiD sequencing system); Roche (e.g., the 454 GS FLX+ and/or GS Junior sequencing systems); or any other sequencing platform of interest.

In certain aspects, a sequencing platform adapter construct includes one or more nucleic acid domains selected from: a domain (e.g., a "capture site" or "capture sequence") that specifically binds to a surface-attached sequencing platform oligonucleotide (e.g., the P5 or P7 oligonucleotides attached to the surface of a flow cell in an Illumina® sequencing system); a sequencing primer binding domain (e.g., a domain to which the Read 1 or Read 2 primers of the Illumina® platform may bind); a barcode domain (e.g., a domain that uniquely identifies the sample source of the nucleic acid being sequenced to enable sample multiplexing by marking every molecule from a given sample with a specific barcode or "tag"); a barcode sequencing primer binding domain (a domain to which a primer used for sequencing a barcode binds); a molecular identification domain (e.g., a molecular index tag, such as a randomized tag of 4, 6, or other number of nucleotides) for uniquely marking molecules of interest to determine expression levels based on the number of instances a unique tag is sequenced; or any combination of such domains. In certain aspects, a barcode domain (e.g., sample index tag) and a molecular identification domain (e.g., a molecular index tag) may be included in the same nucleic acid.

A sequencing platform adapter domain, when present, may include one or more nucleic acid domains of any length and sequence suitable for the sequencing platform of interest. In certain aspects, the nucleic acid domains are from 4 to 200 nts in length. For example, the nucleic acid domains may be from 4 to 100 nts in length, such as from 6 to 75, from 8 to 50, or from 10 to 40 nts in length. According to certain embodiments, the sequencing platform adapter construct includes a nucleic acid domain that is from 2 to 8 nucleotides in length, such as from 9 to 15, from 16 to 22, from 23 to 29, or from 30 to 36 nts in length.

The nucleic acid domains may have a length and sequence that enables a polynucleotide (e.g., an oligonucleotide) employed by the sequencing platform of interest to specifically bind to the nucleic acid domain, e.g., for solid phase amplification and/or sequencing by synthesis of the cDNA insert flanked by the nucleic acid domains. Example nucleic acid domains include the P5 (5'-AATGATACGGCGAC-CACCGA-3') (SEQ ID NO:01), P7 (5'-CAAGCAGAA-GACGGCATACGAGAT-3') (SEQ ID NO:02), Read 1 primer (5'-ACACTCTTTCCCTACACGACGCTCTTCC-GATCT-3') (SEQ ID NO:03) and Read 2 primer (5'-GTGACTGGAGTTCAGACGTGTGCTCTTCCGATCT-3') (SEQ ID NO:04) domains employed on the Illumina®-based sequencing platforms. Other example nucleic acid domains include the A adapter (5'-CCATCT-CATCCCTGCGTGTCTCCGACTCAG-3') (SEQ ID NO:05) and P1 adapter (5'-CCTCTC-TATGGGCAGTCGGTGAT-3') (SEQ ID NO:06) domains employed on the Ion Torrent™-based sequencing platforms. For example, the first strand cDNA primer may include from 3' to 5', a first domain that hybridizes to the template RNA, e.g., an oligo dT domain, a barcode domain, a molecular identifier, a sequencing platform adapter domain, such as a read primer domain (e.g., RP2), and a pre-tagmentation amplification primer binding domain, which pre-tagmentation amplification primer binding domain may be the same as the pre-tagmentation amplification primer binding domain of the template switch oligonucleotide, described in greater detail below. It is noted in this embodiment that the first strand cDNA primer also includes a post-tagmentation amplification primer binding domain, which domain may be a unique domain in the primer or partially or completely overlap with another domain of the primer, such as the RP2 domain, so long as that domain is compatible with respect to the over protocol being performed.

The nucleotide sequences of nucleic acid domains useful for sequencing on a sequencing platform of interest may vary and/or change over time. Adapter sequences are typically provided by the manufacturer of the sequencing platform (e.g., in technical documents provided with the sequencing system and/or available on the manufacturer's website). Based on such information, the sequence of any sequencing platform adapter domains of the template switch oligonucleotide, first strand cDNA primer, amplification primers, and/or the like, may be designed to include all or a portion of one or more nucleic acid domains in a configuration that enables sequencing the nucleic acid insert (corresponding to the template RNA) on the platform of interest.

The first strand cDNA primer may include one or more nucleotides (or analogs thereof) that are modified or otherwise non-naturally occurring. For example, the primer may include one or more nucleotide analogs (e.g., LNA, FANA, 2'-O-Me RNA, 2'-fluoro RNA, or the like), linkage modifications (e.g., phosphorothioates, 3'-3' and 5'-5' reversed linkages), 5' and/or 3' end modifications (e.g., 5' and/or 3' amino, biotin, DIG, phosphate, thiol, dyes, quenchers, etc.), one or more fluorescently labeled nucleotides, or any other feature that provides a desired functionality to the primer that primes cDNA synthesis.

It may be desirable to prevent any subsequent extension reactions which use the double stranded product nucleic acid as a template from extending beyond a particular position in the region of the double stranded product nucleic acid corresponding to the primer. For example, according to certain embodiments, the first strand cDNA primer includes a polymerase blocking modification that prevents a polymerase using the region corresponding to the primer as a template from polymerizing a nascent strand beyond the modification. Useful modifications include, but are not limited to, an abasic lesion (e.g., a tetrahydrofuran derivative), a nucleotide adduct, an iso-nucleotide base (e.g., isocytosine, isoguanine, and/or the like), and any combination thereof. Such blocking modifications may be included in any of the nucleic acid reagents used when practicing the methods of the present disclosure, including first strand cDNA primer, the template switch oligonucleotide, first and second amplification, e.g., PCR, primers used for amplifying the first-strand cDNA to produce the product double stranded cDNA, amplification primers used for PCR amplification of tagmentation products, and any combination thereof. In some instances, primers employed in methods of the invention, such as amplification, e.g., PCR, primers, include a ligation block. Ligation blocks of interest that may be present in a given primer, as desired, include but are not limited to: amine, inverted T, and Biotin-TEG.

As set forth above, the subject methods include combining a template switch oligonucleotide into the reaction mixture. By "template switch oligonucleotide" is meant an oligonucleotide template to which a polymerase switches from an initial template (e.g., a template RNA) during a nucleic acid polymerization reaction. In this regard, a template RNA may be referred to as a "donor template" and the template switch oligonucleotide may be referred to as an "acceptor template." As used herein, an "oligonucleotide" can refer to a single-stranded multimer of nucleotides from 2 to 500 nts, e.g., 2 to 200 nts. Oligonucleotides may be synthetic or may be made enzymatically, and, in some embodiments, are 10 to 50 nts in length. Oligonucleotides may contain ribonucleotide monomers (i.e., may be oligoribonucleotides or "RNA oligonucleotides") or deoxyribonucleotide monomers (i.e., may be oligodeoxyribonucleotides or "DNA oligonucleotides"). Oligonucleotides may be 10 to 20, 21 to 30, 31 to 40, 41 to 50, 51 to 60, 61 to 70, 71 to 80, 80 to 100, 100 to 150 or 150 to 200, up to 500 or more nts in length, for example.

The reaction mixture includes the template switch oligonucleotide at a concentration sufficient to permit template switching of the polymerase from the template RNA to the template switch oligonucleotide. For example, the template switch oligonucleotide may be added to the reaction mixture at a final concentration of from 0.01 to 100 µM, such as from 0.1 to 10 µM, such as from 0.5 to 5 µM, including 2 to 3 µM.

The template switch oligonucleotide may include one or more nts (or analogs thereof) that are modified or otherwise non-naturally occurring. For example, the template switch oligonucleotide may include one or more nucleotide analogs (e.g., LNA, FANA, 2'-O-Me RNA, 2'-fluoro RNA, or the like), linkage modifications (e.g., phosphorothioates, 3'-3' and 5'-5' reversed linkages), 5' and/or 3' end modifications (e.g., 5' and/or 3' amino, biotin, DIG, phosphate, thiol, dyes, quenchers, etc.), one or more fluorescently labeled nts, or any other feature that provides a desired functionality to the template switch oligonucleotide. Any desired nucleotide analogs, linkage modifications and/or end modifications may be included in any of the nucleic acid reagents used when practicing the methods of the present disclosure, including the first strand cDNA primer, the template switch oligonucleotide, the pre-tagmentation primers used for amplifying, e.g., PCR amplifying, the first-strand cDNA to produce the product double stranded cDNA, the post-tagmentation primers used for amplification of tagmentation products, and any combination thereof.

The template switch oligonucleotide includes a 3' hybridization domain and a 5' pre-tagmentation primer binding domain (which may also be referred to as a second strand synthesis/pre-tagmentation amplification primer binding domain). The 3' hybridization domain may vary in length, and in some instances ranges from 2 to 10 nts in length, such as from 3 to 7 nts in length. The sequence of the 3' hybridization domain, i.e., template switch domain, may be any convenient sequence, e.g., an arbitrary sequence, a heteropolymeric sequence (e.g., a hetero-trinucleotide) or homopolymeric sequence (e.g., a homo-trinucleotide, such as G-G-G), or the like. Examples of 3' hybridization domains and template switch oligonucleotides are further described in U.S. Pat. No. 5,962,272 and published PCT application publication no. WO2015027135, the disclosures of which are herein incorporated by reference.

In addition to a 3' hybridization, i.e., template switch, domain, the template switch oligonucleotide can include a pre-tagmentation primer binding domain (i.e., pre-tagmentation primer binding site, which may include a defined nucleotide sequence 5' of the 3' hybridization domain of the template switch oligonucleotide), that enables second strand synthesis and/or amplification, e.g., PCR amplification, of the first strand cDNA product nucleic acid. For example, the template switch oligonucleotide may include a sequence, where subsequent to generating the first strand cDNA product nucleic acid, second strand synthesis is performed using a primer that has that sequence. The second strand synthesis produces a second strand DNA complementary to the first strand cDNA (i.e., first single product nucleic acid). Alternatively, or additionally, the product nucleic acid may be amplified using a primer pair in which one of the primers has that sequence. According to certain embodiments, the template switch oligonucleotide includes a first post-tagmentation (e.g., PCR) primer binding domain, e.g., for use in amplification of a tagemented product, e.g., as described in greater detail below. This post-tagmentation primer binding domain may be positioned, e.g., between the pre-tagmentation primer binding domain and the 3' hybridization domain.

According to certain embodiments, the template switch oligonucleotide includes a modification that prevents the polymerase from switching from the template switch oligonucleotide to a different template nucleic acid after synthesizing the compliment of the 5' end of the template switch oligonucleotide (e.g., a 5' adapter sequence of the template switch oligonucleotide). Useful modifications include, but are not limited to, an abasic lesion (e.g., a tetrahydrofuran derivative), a nucleotide adduct, an iso-nucleotide base (e.g., isocytosine, isoguanine, and/or the like), and any combination thereof.

In addition to the above components, the template switch oligonucleotide may further include a number of additional components or domains positioned between the 5' and 3' domains described above, such as but not limited to: a first post-tagmentation amplification primer binding domain (e.g., in those embodiments where such a domain is not present on the first strand cDNA synthesis primer), barcode domains, unique molecular identifier domains, a sequencing platform adapter construct domains, etc., where these domains may be as described above.

As described above, the subject methods include combining dNTPs into the reaction mixture. In certain aspects, each of the four naturally-occurring dNTPs (dATP, dGTP, dCTP and dTTP) are added to the reaction mixture. For example, dATP, dGTP, dCTP and dTTP may be added to the reaction mixture such that the final concentration of each dNTP is from 0.01 to 100 mM, such as from 0.1 to 10 mM, including 0.5 to 5 mM (e.g., 1 mM). According to one embodiment, at least one type of nucleotide added to the reaction mixture is a non-naturally occurring nucleotide, e.g., a modified nucleotide having a binding or other moiety (e.g., a fluorescent moiety, biotin) attached thereto, a nucleotide analog, or any other type of non-naturally occurring nucleotide that finds use in the subject methods or a downstream application of interest.

Any nucleic acids that find use in practicing the methods of the present disclosure (e.g., the first strand cDNA primer, the template switch oligonucleotide, a second strand synthesis primer, one or more primers for amplifying the double stranded product nucleic acid, and/or the like) may include any useful nucleotide analogues and/or modifications, including any of the nucleotide analogues and/or modifications described herein.

Once the double stranded product nucleic acid, e.g., that includes first strand cDNA, is produced, the methods include using the product nucleic acid as a template for second-strand synthesis and/or amplification (e.g., for subsequent sequencing of the amplicons). According to one embodiment, the methods include contacting the product nucleic acid with primers that hybridize to the pre-tagmentation amplification primer binding domains, where these domains may be on the ends of the double-stranded cDNA, under amplification conditions, such as PCR amplification conditions, sufficient to produce a product double stranded cDNA. Depending on the embodiment, a single primer may be used for this step, e.g., where the pre-tagmentation amplification primer binding domains are the same, or different, where the pre-tagmentation amplification primer binding domains are different and first and second amplification primers complementary to different pre-tagmentation amplification primer binding domains are employed. Amplification conditions that may be employed include the addition of the one or more primers (e.g., as described above) and dNTPs. The conditions may include combining a thermostable polymerase (e.g., a Taq, Pfu, Tfl, Tth, Tli, and/or other thermostable polymerase)—in addition to the template switching polymerase—into the reaction mixture. Alternatively, the template switching polymerase may be a thermostable polymerase. Either of these embodiments find use, e.g., when it is desirable to achieve production and amplification (e.g., amplification with or without further adapter addition) of the double stranded product nucleic acid in a single container, such as a tube, well, microfluidic chamber, droplet, nanowell, etc. For example, the contents of the single container may be placed under conditions suitable for the template switch polymerization reaction to occur (as described elsewhere herein), followed by placing the reaction contents under thermocycling conditions (e.g., denaturation, primer annealing, and polymerization conditions) in which the first-strand cDNA is amplified using primers complementary to the first and second primer binding domains and the thermostable polymerase present in the single container. Due to its thermostability, the thermostable polymerase will retain its activity even when present during the cDNA synthesis phase of this embodiment.

The first and second amplification primers complementary to the first and second primer binding domains that are employed in this step may vary, and in some instances have the same sequence. A sequence/primer of interest is the 5' Primer II A (Takara Bio USA, Inc., Mountain View, Calif.). According to one embodiment, the first and second amplification primers are both the 5' Primer II A.

Figure 2:
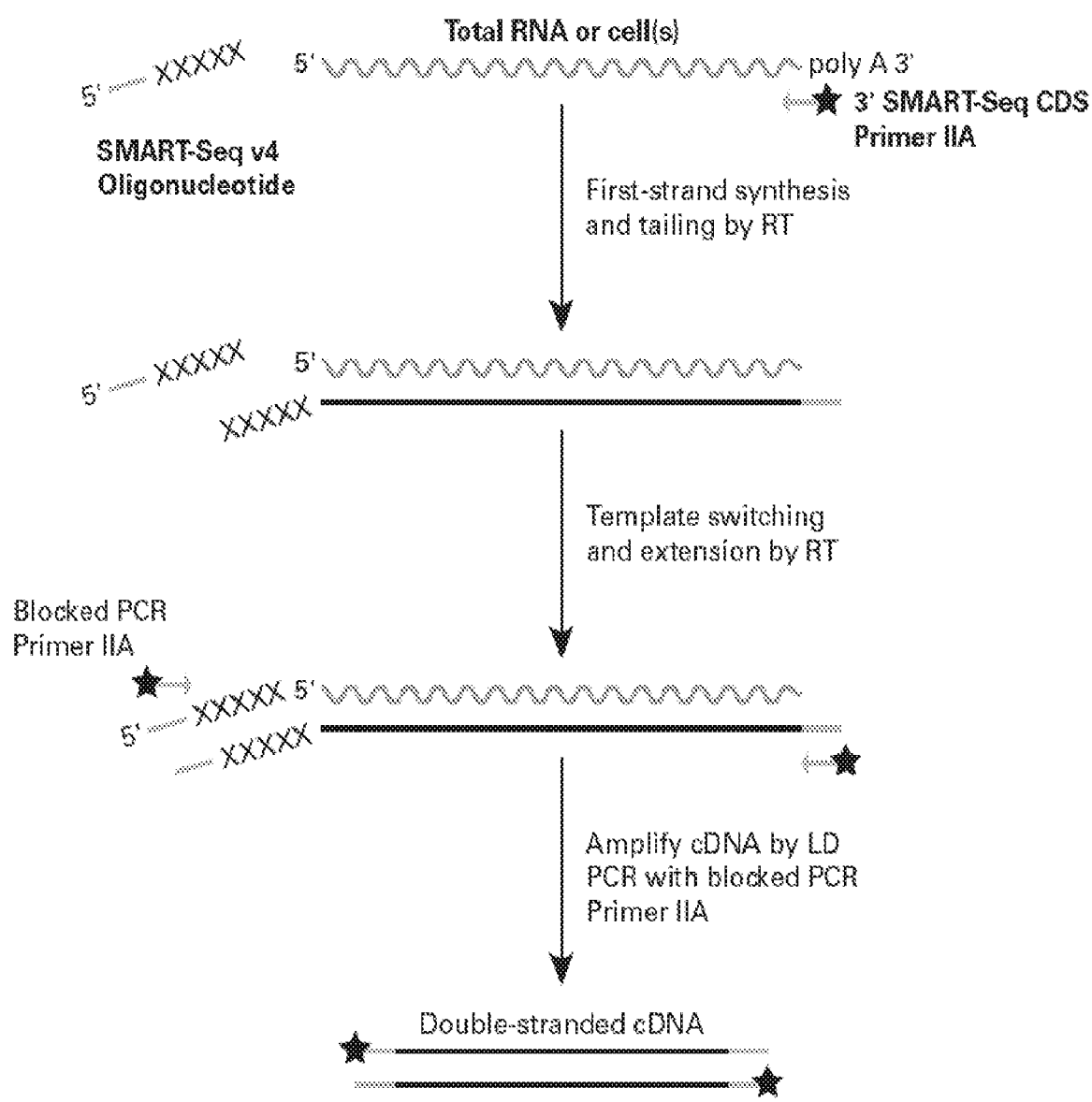
FIG. 2 schematically illustrates a template switch-based method for producing a product double stranded cDNA according to one embodiment of the present disclosure.

Amplification, e.g., PCR amplification, results in the production of a product double stranded cDNA. A method of producing a product double stranded cDNA according to one embodiment of the present disclosure is schematically illustrated in FIG. 2. As illustrated in FIG. 2, a RNA sample that includes an mRNA (wavy line) is combined with a first strand cDNA primer (in this example, a 3' SMART-Seq CDS Primer IIA), a template switch oligonucleotide (in this example, a SMART-Seq oligonucleotide), a reverse transcriptase (not shown) and dNTPs (not shown). Non-templated nucleotides (indicated by Xs) are added by the reverse transcriptase when it reaches the 5' end of the mRNA during cDNA synthesis. Template switching occurs from the template mRNA to the template switch oligonucleotide which has a 3' hybridization domain complementary to the non-templated nucleotides of the first-strand cDNA. In this example, the 5' end of the mRNA is captured, allowing for downstream amplification and enrichment of full-length cDNA, e.g., by LD PCR (Long Distance PCR). In this example, locked nucleic acid (LNA) modifications to the template switching oligonucleotide and ligation-inhibiting blocks on the priming oligonucleotides (black stars on the 5' ends of the priming oligonucleotides) are included. The components are combined in a reaction mixture under conditions sufficient to produce a double stranded product nucleic acid including a template mRNA and the template switch oligonucleotide each hybridized to adjacent regions of a first strand complementary deoxyribonucleic acid (cDNA). Product double stranded cDNA is produced by contacting the double stranded product nucleic acid with amplification primers complementary to PCR primer binding domains present in the first strand cDNA primer and template switch oligonucleotide. In this example, a single species of primer (here, PCR Primer IIA) is capable of amplifying the double stranded product nucleic acid by virtue of the first strand cDNA primer and template switch oligonucleotide each having a PCR primer binding domain complementary to PCR Primer IIA.

Following production of the product double stranded cDNA, product double stranded cDNA is tagmented with one or more transposomes including a transposase and a transposon nucleic acid, where the transposon nucleic acid includes a transposon end domain for binding to the transposon protein and a second post-tagmentation amplification primer binding domain (e.g., a post-tagmentation PCR amplification primer binding domain), to produce a tagmented sample. In certain aspects, the second post-tagmentation amplification primer binding domain comprises a NGS read primer domain, e.g., a read primer domain that is different from any read primer domain present in the first-strand cDNA primer, or template switch oligonucleotide.

Transposomes employed in methods of the present disclosure include a transposase and a transposon nucleic acid that includes a transposon end domain and a post-tagmentation amplification primer binding domain. These domains are defined functionally and so may be one in the same sequence or may be different sequences, as desired. The domains may also overlap, such that part of the post-tagmentation amplification primer binding domain may be present in the transposon end domain.

A "transposase" means an enzyme that is capable of forming a functional complex with a transposon end domain-containing composition (e.g., transposons, transposon ends, transposon end compositions) and catalyzing insertion or transposition of the transposon end-containing composition into the double-stranded target DNA with which it is incubated in an in vitro transposition reaction. Transposases that find use in practicing the methods of the present disclosure include, but are not limited to, Tn5 transposases, Tn7 transposases, and Mu transposases. The transposase may be a wild-type transposase. In other aspects, the transposase includes one or more modifications (e.g., amino acid substitutions) to improve a property of the transposase, e.g., enhance the activity of the transposase. For example, hyperactive mutants of the Tn5 transposase having substitution mutations in the Tn5 protein (e.g., E54K, M56A and L372P) have been developed and are described in, e.g., Picelli et al. (2013) *Genome Research* 24:2033-2040. Additional Tn5 substitution mutations include, but are not limited to: Y41H; T47P; E54V, E110K, P242A, E344A, and E345A. A given Tn5 mutant may include one or more substitutions, where combinations of substitutions that may be present include, but are not limited to: T47P, M56A and L372P; TT47P, M56A, P242A and L372P; and M56A, E344A and L372P.

The term "transposon end domain" means a double-stranded DNA that consists only of the nucleotide sequences (the "transposon end sequences") that are necessary to form the complex with the transposase or integrase enzyme that is functional in an in vitro transposition reaction. A transposon end domain forms a "complex" or a "synaptic complex" or a "transposome complex" or a "transposome composition" with a transposase or integrase that recognizes and binds to the transposon end domain, and which complex is capable of inserting or transposing the transposon end domain into target DNA with which it is incubated in an in vitro transposition reaction. A transposon end domain exhibits two complementary sequences consisting of a "transferred transposon end sequence" or "transferred strand" and a "non-transferred transposon end sequence," or "non-transferred strand." For example, one transposon end domain that forms a complex with a hyperactive Tn5 transposase (e.g., EZ-Tn5 Transposase, EPICENTRE Biotechnologies, Madison, Wis., USA) that is active in an in vitro transposition reaction includes a transferred strand that exhibits a "transferred transposon end sequence" as follows: 5' AGATGTGTATAAGAGACAG 3', (SEQ ID NO:07) and a non-transferred strand that exhibits a "non-transferred transposon end sequence" as follows: 5' CTGTCTCTTATACA-CATCT 3' (SEQ ID NO:8). The 3'-end of a transferred strand is joined or transferred to target DNA in an in vitro transposition reaction. The non-transferred strand, which exhibits a transposon end sequence that is complementary to the transferred transposon end sequence, is not joined or transferred to the target DNA in an in vitro transposition reaction. The sequence of the particular transposon end domain to be employed when practicing the methods of the present disclosure will vary depending upon the particular transposase employed. For example, a Tn5 transposon end domain may be included in the transposon nucleic acid when used in conjunction with a Tn5 transposase.

In addition to the transposon end domain, the transposon nucleic acid also includes a second post-tagmentation amplification primer binding domain. In some instances, the second post-tagmentation amplification primer binding domain includes a sequencing platform adapter construct domain, e.g., as described above. This domain may be a nucleic acid domain selected from a domain (e.g., a "capture site" or "capture sequence") that specifically binds to a surface-attached sequencing platform oligonucleotide (e.g., the P5 or P7 oligonucleotides attached to the surface of a flow cell in an Illumina® sequencing system), a sequencing primer binding domain (e.g., a domain to which the Read 1 or Read 2 primers of the Illumina® platform may bind), a barcode domain (e.g., a domain that uniquely identifies the sample source of the nucleic acid being sequenced to enable sample multiplexing by marking every molecule from a given sample with a specific barcode or "tag"), a barcode sequencing primer binding domain (a domain to which a primer used for sequencing a barcode binds), a molecular identification domain, or any combination of such domains. In certain aspects, the sequencing platform adapter construct domain (e.g., which may include post-tagmentation amplification primer binding domain) of the transposon nucleic acid is different from the sequencing platform adapter construct domain (e.g., which may include a post-tagmentation amplification primer binding domain) of the first strand cDNA. Such embodiments find use, e.g., where one wishes to produce a library of nucleic acids with one end having one or more sequencing platform adapter sequences and the second end having one or more sequencing platform adapter sequences different from the first end. Having ends with different adapter sequences is useful, e.g., for subsequent solid phase amplification (e.g., cluster generation using the surface-attached P5 and P7 primers in an Illumina®-based sequencing system), DNA sequencing (e.g., using the Read 1 and Read 2 primers in an Illumina®-based sequencing system), and any other steps performed by a sequencing platform requiring different adapter sequences at opposing ends of the nucleic acid to be sequenced. Having different ends is also useful in providing strand specific information, since the directionality of the sequenced strand is defined by the different ends.

When it is desirable to prepare transposomes for the tagmentation step, any suitable transposome preparation approach may be used, and such approaches may vary depending upon, e.g., the specific transposase and transposon nucleic acids to be employed. For example, the transposon nucleic acids and transposase may be incubated together at a suitable molar ratio (e.g., a 2:1 molar ratio, a 1:1 molar ratio, a 1:2 molar ratio, or the like) in a suitable buffer. According to one embodiment, when the transposase is a Tn5 transposase, preparing transposomes may include incubating the transposase and transposon nucleic acid at a 1:1 molar ratio in 2x Tn5 dialysis buffer for a sufficient period of time, such as 1 hour.

Tagmenting the product double stranded cDNA includes contacting the double stranded cDNA with a transposome under tagmentation conditions. Such conditions may vary depending upon the particular transposase employed. In some instances, the conditions include incubating the transposomes and tagged extension products in a buffered reaction mixture (e.g., a reaction mixture buffered with Tris-acetate, or the like) at a pH of from 7 to 8, such as pH 7.5. The transposome may be provided such that about a molar equivalent, or a molar excess, of the transposon is present relative to the tagged extension products. Suitable temperatures include from 32° to 42° C., such as 37° C. The reaction is allowed to proceed for a sufficient amount of time, such as from 5 minutes to 3 hours. The reaction may be terminated by adding a solution (e.g., a "stop" solution), which may include an amount of SDS and/or other transposase reaction termination reagent suitable to terminate the reaction. Protocols and materials for achieving fragmentation of nucleic acids using transposomes are available and include, e.g., those provided in the EZ-Tn5™ transpose kits available from EPICENTRE Biotechnologies (Madison, Wis., USA).

The resultant tagmented sample is then subjected to amplification conditions, e.g., PCR amplification conditions, using post-tagmentation first and second amplification, e.g., PCR, primers. These post-tagmentation first and second amplification primers may vary, and in some instances include sequencing platform adapter domains, e.g., a first primer including a first post-tagmentation amplification primer domain, a first NGS indexing domain and a first NGS adapter domain; and a second primer including a second post-tagmentation amplification primer domain, a second NGS indexing domain and a second NGS adapter domain, to produce a NGS library. The sequencing platform adapter construct(s) may include any of the nucleic acid domains described elsewhere herein (e.g., a domain that specifically binds to a surface-attached sequencing platform oligonucleotide, a sequencing primer binding domain, a barcode domain, a barcode sequencing primer binding domain, a molecular identification domain, or any combination thereof). Such embodiments find use, e.g., where nucleic acids of the tagmented sample do not include all of the adapter domains useful or necessary for sequencing in a sequencing platform of interest, and the remaining adapter domains are provided by the primers used for the amplification of the nucleic acids of the tagmented sample.

In some instances, following production of double stranded cDNA and prior to tagmentation, the method includes pooling the double stranded product cDNA with one or more additional double stranded product cDNAs (e.g., obtained from a different starting RNA source, e.g., cell) to produce a pooled cDNA sample. For example, the combining and contacting steps described above may be performed in parallel for 2 or more, 3 or more, 4 or more, 5 or more, 6 or more, 7 or more, 8 or more, 9 or more, 10 or more, 11 or more, 12 or more, 20 or more, 30 or more, 40 or more, 50 or more (e.g., 96), 100 or more, 1000 or more, 10,000, 25,000 or more, 50,000 or more, 100,000 or more, 250,000 or more, 500,000 or more, 1,000,000 or more different starting RNA sources, where in some instances the number of different starting RNA sources is 1,000,000 or less, such as 500,000 or less, 250,000 or less, 100,000 or less, 50,000 or less, 25,000 or less, 10,000 or less, such as 5,000 or less, including 2,000 or less. In certain aspects, the different starting RNA sources are single cells (e.g., circulating tumor cells or any other single cells of interest). The single cells may be obtained from the same individual or different individuals. According to certain embodiments, the different starting RNA sources are RNA samples obtained from different individuals, e.g., different human patients or other human individuals for whom it is desirable to obtain nucleic acid (e.g., RNA or DNA) sequence information. In certain aspects, the double stranded product cDNAs are tagged during their production with a unique source identifier (e.g., a cell barcode) corresponding to the starting RNA sample from which the product cDNAs were generated. The resultant double stranded product cDNAs produced in parallel may then be pooled prior to tagmentation. Such a pooling step may include combining each double stranded product cDNA sample (or aliquots thereof) to be pooled into a single container (e.g., a single tube or other container, e.g., well, microfluidic chamber, droplet, nanowell, etc). The pooled cDNA sample is then tagmented, e.g., as described above. Upon sequencing the tagmented sample, individual sequencing reads can be traced back to particular starting RNA samples using the source, e.g., cell barcode, enabling multiplexed sequencing. Details regarding barcode-based multiplexed sequencing are described, e.g., in Wong et al. (2013) Curr. Protoc. Mol. Biol. Chapter 7:Unit 7.11.

According to certain embodiments, the methods of preparing NGS libraries are end-capture methods for quantifying RNA (e.g., mRNA transcripts), e.g., for differential expression analysis. In certain aspects, the end-capture methods capture the 3' ends of RNAs, e.g., where end-capture is facilitated by the presence of a first post-tagmentation amplification primer binding site in the first strand cDNA primer and a second post-tagmentation PCR primer binding site introduced by tagmentation. In other aspects, the end-capture methods capture the 5' ends of RNAs, e.g., where end-capture is facilitated by the presence of a first post-tagmentation amplification primer binding site in the template switch oligonucleotide and a 3' second post-tagmentation PCR primer binding site introduced by tagmentation.

Figure 3A:
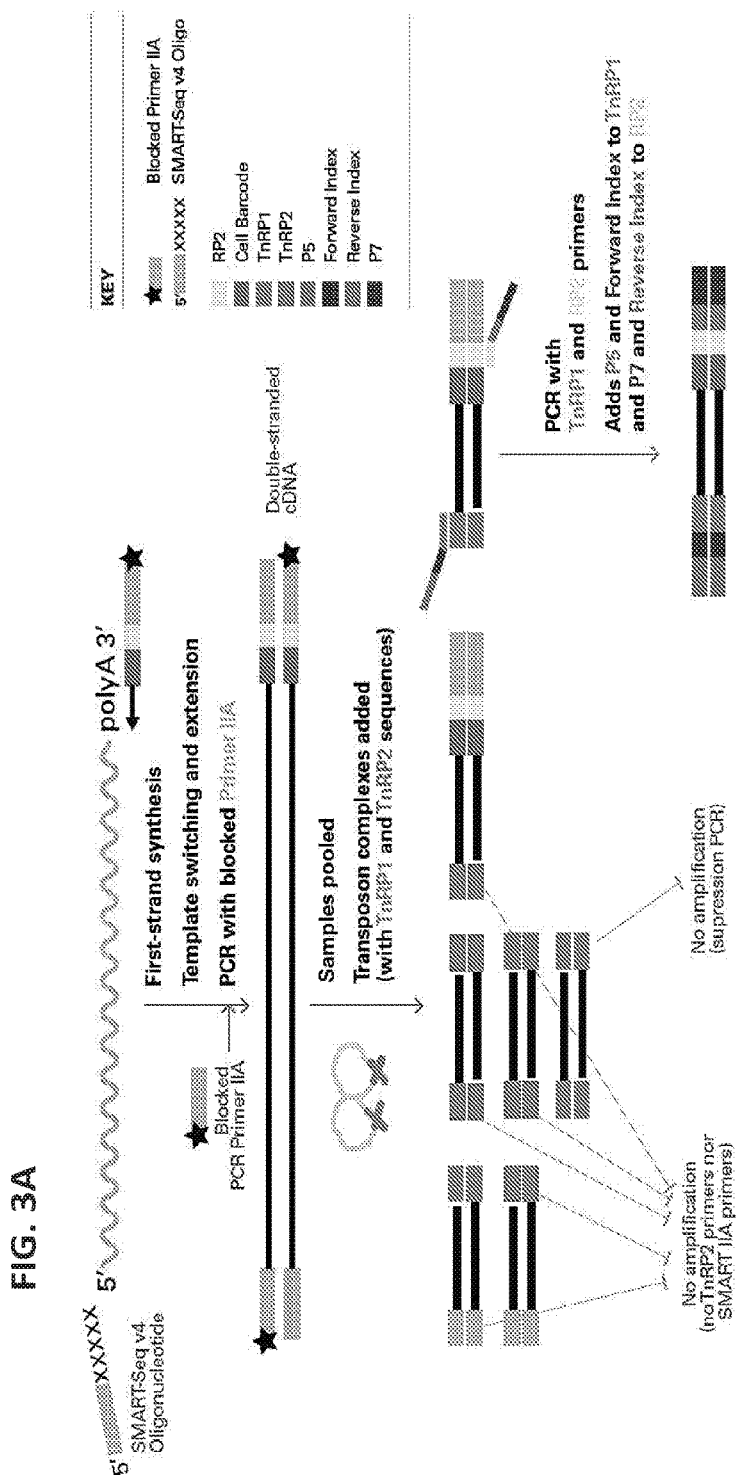
FIG. 3A schematically illustrates the preparation of a NGS library from a RNA sample according to one embodiment of the present disclosure.

An end-capture NGS library preparation method according to one embodiment of the present disclosure is schematically illustrated in FIG. 3A. The method includes combining a RNA sample, a first strand cDNA primer including a first pre-tagmentation amplification primer binding domain, a template switch oligonucleotide including a 3' hybridization domain and a 5' second pre-tagmentation amplification primer binding domain (where both the first and second pre-tagmentation primer binding domains bind to the same primer, in this case "Blocked PCR Primer IIA"), a reverse transcriptase (not shown), and dNTPs (not shown), in a reaction mixture under conditions sufficient to produce a double stranded product nucleic acid (not shown) including a template mRNA and the template switch oligonucleotide each hybridized to adjacent regions of a first strand cDNA. In this example, the RNA sample includes an mRNA (polyA+) template, and the first strand cDNA primer includes an oligo-dT 3' hybridization domain, a cell barcode, a sequencing adapter domain (here, an Illumina® Read Primer 2 sequence—also acting as a first post-tagmentation primer binding domain), a pre-tagmentation amplification primer binding domain (here, a domain that binds the Clontech® Primer IIA), and a blocking modification (black star). During first strand synthesis, the reverse transcriptase template switches from the template mRNA to a template switch oligonucleotide (in this example, the Clontech SMART-Seq v4 template switch oligonucleotide) that includes a 3' hybridization domain that includes an LNA and a 5' domain that a second pre-tagmentation amplification primer binding domain. In this example, the second pre-tagmentation amplification primer binding domain (a domain that binds the Clontech® Primer IIA) is the same as the first pre-tagmentation primer binding domain. After first-strand synthesis, the cDNA is amplified, e.g., via PCR, using a blocked Clontech® Primer IIA primer to generate product double stranded cDNA (labeled "Double-stranded cDNA" in FIG. 3A).

In the example shown in FIG. 3A the product double stranded cDNA is pooled with one or more other product double stranded cDNA generated in parallel using one or more different RNA samples, e.g., from one or more different single cells. For example, the pooling may include combining an aliquot of the product double stranded cDNA with aliquot(s) of one or more other product double stranded cDNA in a single tube or other container, e.g., well, microfluidic chamber, droplet, nanowell, etc.

The pooled sample product double stranded cDNA is then subjected to tagmentation using one or more transposomes that include a transposase and a transposon nucleic acid including a transposon end domain and one or more second post-tagmentation amplification, e.g., PCR, primer binding domains. In this example, transposomes including a Tn5 transposase and the Illumina® Nextera® TnRP1 or TnRP2 sequences (where TnRP1 is used as a second post-tagmentation amplification primer binding domain) are used (FIG. 3A, FIG. 1).

The resulting types of tagmentation products of the tagmented sample are shown. Following tagmentation, amplification designed for 3' end capture is carried out using post-tagmentation amplification primers that bind to the post-tagmentation amplification, e.g., PCR amplification, primer domains. In this example, amplification is carried out using a first post-tagmentation amplification primer that includes a post-tagmentation amplification primer binding domain, a first NGS indexing domain and a NGS adapter domain. In this example, the first post-tagmentation amplification primer binding domain binds to the Read Primer 2 sequence added during first-strand cDNA synthesis, the first indexing domain is a reverse index sequence, and the NGS adapter domain is the Illumina® P7 sequencing adapter. The other amplification primer is a second amplification primer that includes a second post-tagmentation amplification primer binding domain, a second NGS indexing domain and a NGS adapter domain. In this example, the second post-tagmentation amplification primer binding domain binds to the TnRP1 sequence added to a subpopulation of the pooled product double stranded cDNAs during tagmentation, the first indexing domain is a forward index sequence, and the NGS adapter domain is the Illumina® P5 sequencing adapter. Only the tagmentation products having the 3' RP2 sequence and a TnRP1 sequence (provided during tagmentation) will be amplified, as shown in FIG. 3A.

Figure 3B:
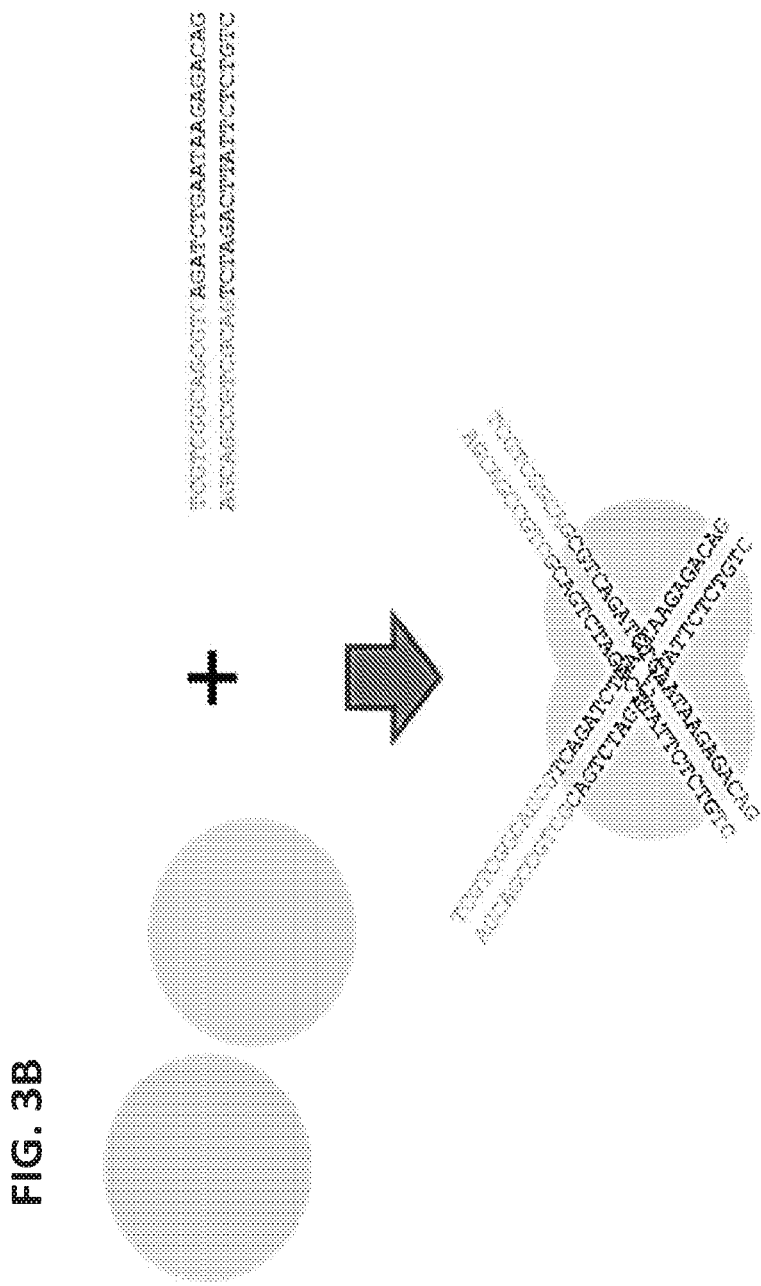
FIG. 3B schematically illustrates the assembly of a transposome according to an embodiment of the present disclosure.
Figure 3C:
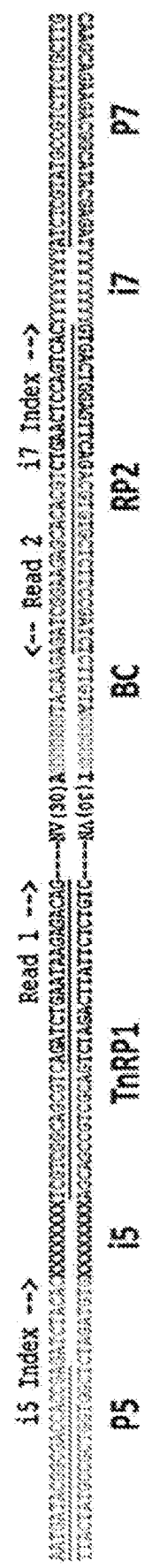
FIG. 3C schematically illustrates a nucleic acid of the NGS library produced according to the example embodiment illustrated in panel A.

In the example shown in FIG. 3A, amplification of the tagmentation products completes the preparation of the NGS library. In this example, the nucleic acids in the library (shown on the bottom right of panel A) are suitable for sequencing on an Illumina® sequencing system and include: the P5 adapter sequence; a forward index sequence; the TnRP1 sequence; an insert corresponding to a 3' end of the template mRNA; a source barcode sequence (e.g., corresponding to a single cell or individual, etc.); the RP2 sequence, a reverse index sequence; and a P7 adapter sequence. The nucleic acid sequence of such a product is shown in FIG. 3C.

It will be understood that numerous variations to the above example end-capture method are possible. Instead of capturing 3' ends of RNAs, for example, the method may be used to capture 5' ends of RNAs. Capturing the 5' ends of RNAs finds use, e.g., for 5' end mutation or splice variant analysis, etc. 5' end capture may be carried out, e.g., by including a post-tagmentation primer binding domain (e.g., an RP2 sequence) in the template switch oligonucleotide, rather than in the first strand cDNA primer. According to this variation, post-tagmentation amplification may be carried out using an post-tagmentation amplification primer that binds to the first post-tagmentation primer binding domain domain originally present in the template switch oligonucleotide, in conjunction with a post-tagmentation amplification primer that binds to post-tagmentation primer binding domain, e.g., a TnRP1 or TnRP2 sequence, added during a tagmentation step.

Other variations include, e.g., replacing Illumina®-specific sequencing domains in the various primers/oligonucleotides with sequencing domains required by sequencing systems from, e.g., Ion Torrent™ (e.g., the Ion PGM™ and Ion Proton™ sequencing systems); Pacific Biosciences (e.g., the PACBIO RS II sequencing system); Life Technologies™ (e.g., a SOLiD sequencing system); Roche (e.g., the 454 GS FLX+ and GS Junior sequencing systems); or any other sequencing platform of interest.

In another variation, rather than using two types of transposomes (such as the TnRP1 or TnRP2 transposomes employed in the example above), a single type of transposome (having a single type of second post-tagmentation amplification, e.g., PCR, primer binding domain) could be employed. The assembly of one such modified transposome is schematically illustrated in FIG. 3B, where the Tn5 transposase is shown as solid circles before and after loading with the transposon nucleic acids. Amplification of the desired tagmentation products could be carried out using a primer that binds to the single type of post-tagmentation amplification, e.g., PCR, primer binding domain provided by the transposome, in conjunction with a primer that binds to a first post-tagmentation amplification, e.g., PCR, primer binding domain that has been added during an earlier step (e.g., first strand synthesis or amplification of the double stranded product nucleic acid, etc.).

Figure 3D:
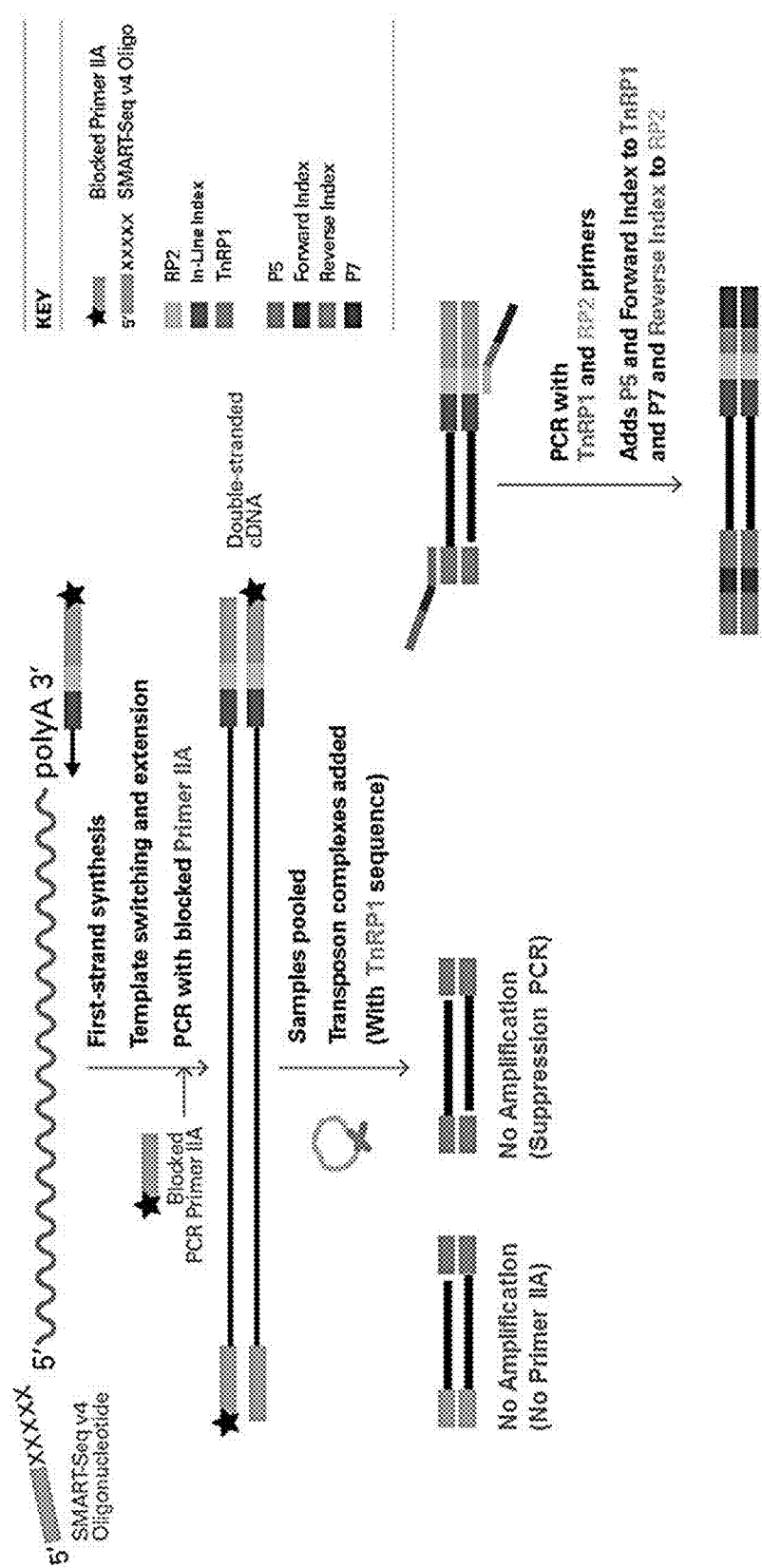
FIG. 3D schematically illustrates the preparation of a NGS library from a RNA sample according to one embodiment of the present disclosure that employs a single transposome.

FIG. 3D schematically illustrates the preparation of a NGS library from an RNA sample according to one embodiment of the present disclosure that employs a single transposome. As shown in FIG. 3D, cDNA (black) is synthesized from template RNA using a blocked (black star) and modified oligo(dT) first strand cDNA synthesis primer that includes a source barcode, e.g., cell barcode (magenta) and a first post-tagmentation primer binding domain (in this case part of the Illumina read primer 2 sequence (RP2, yellow), positioned between the a 3' poly A domain (black arrow) and a 5' pre-tagmentation amplification primer binding domain (in this case the SMART IIA sequence (green)). The SMART IIA sequence is used as a primer binding domain during pre-tagmentation cDNA amplification, the Illumina RP2 sequence is used as a primer binding domain during post-tagmentation library amplification (i.e., it functions as the first post-tagmentation primer binding domain), and the source barcode (e.g., cell barcode) is used for de-multiplexing pooled samples during analysis. The process works as follows: first, a reverse transcriptase (e.g., SMARTScribe™ reverse transcriptase) copies the RNA template by extending from the modified oligo dT primer (CDS primer). Upon reaching the 5' end of the template RNA, the reverse transcriptase switches from the mRNA (blue wavy line) to the SMART-Seq v4 Oligonucleotide (green). After reverse transcription, the full-length cDNA is amplified by PCR with blocked Primer IIA primers that bind to the corresponding pre-tagmentation amplification primer binding domains in the cDNA. After cDNA amplification, the presence of the in-line source, e.g., cell barcode (magenta). allows for pooling. The pooled samples are tagmented using a single transposome and the Illumina Nextera read primer 1 sequence is added by the Nextera Tn5 transposon (TnRP1, orange). The 3' ends of the original mRNA are captured by selective PCR amplification with post-tagmentation primers that bind to the RP2 and TnRP1 sequences (which function as the first and second post-tagmentation primer binding domains, respectively). Other products of the transposon-based reaction are not amplified, either because they lack all the necessary primer binding domains for amplification or because of suppression PCR. In this example, the nucleic acids in the library (shown on the bottom right) are suitable for sequencing on an Illumina® sequencing system and include: the P5 adapter sequence (pink); a forward index sequence (dark blue); the TnRP1 sequence (orange); an insert corresponding to the template mRNA; a source barcode (magenta) (e.g., corresponding to a single cell or individual); the RP2 sequence (yellow), a reverse index sequence (light blue); and a P7 adapter sequence (purple).

In a further variation, rather than using one or two types of transposomes (such as the TnRP1 or TnRP2 transposomes employed in the example above), 3 or more different types of transposomes may be employed for tagmentation. For example, 3 or more, 4 or more, 5 or more, 6 or more, 7 or more, 8 or more, 9 or more, 10 or more, 20 or more, 50 or more, or 100 or more different types of transposomes having different post-tagmentation amplification, e.g., PCR, primer binding domains could be employed. Tagmentation products of interest in such a tagmented sample may be amplified using a primer that binds to a post-tagmentation amplification, e.g., PCR, primer binding domain of a particular type of transposome, in conjunction with a primer that binds to a post-tagmentation amplification, e.g., PCR, primer binding domain added during an earlier step (e.g., first strand synthesis or amplification of the double stranded product nucleic acid, etc.), such as described above.

In some aspects of the invention, the methods include the step of obtaining single cells. Obtaining single cells may be done according to any convenient protocol. A single cell suspension can be obtained using standard methods known in the art including, for example, enzymatically using trypsin or papain to digest proteins connecting cells in tissue samples or releasing adherent cells in culture, or mechanically separating cells in a sample. Single cells can be placed in any suitable reaction vessel in which single cells can be treated individually. For example a 96-well plate, 384 well plate, or a plate with any number of wells such as 2000, 4000, 6000, or 10000 or more—The multi-well plate can be part of a chip and/or device. The present disclosure is not limited by the number of wells in the multi-well plate. In various embodiments, the total number of wells on the plate is from 100 to 200,000, or from 5000 to 10,000. In other embodiments the plate comprises smaller chips, each of which includes 5,000 to 20,000 wells. For example, a square chip may include 125 by 125 nanowells, with a diameter of 0.1 mm.

The weds (e.g., nanowells) in the multi-well plates may be fabricated in any convenient size, shape or volume. The well may be 100 µm to 1 mm in length, 100 µm to 1 mm in width, and 100 µm to 1 mm in depth. In various embodiments, each nanowell has an aspect ratio (ratio of depth to width) of from 1 to 4. In one embodiment, each nanowell has an aspect ratio of 2. The transverse sectional area may be circular, elliptical, oval, conical, rectangular, triangular, polyhedral, or in any other shape. The transverse area at any given depth of the well may also vary in size and shape.

In certain embodiments, the wells have a volume of from 0.1 nl to 1 µl. The nanowell may have a volume of 1 µl or less, such as 500 nl or less. The volume may be 200 nl or less, or 100 nl or less. In an embodiment, the volume of the nanowell is 100 nl. Where desired, the nanowell can be fabricated to increase the surface area to volume ratio, thereby facilitating heat transfer through the unit, which can reduce the ramp time of a thermal cycle. The cavity of each well (e.g., nanowell) may take a variety of configurations. For instance, the cavity within a well may be divided by linear or curved walls to form separate but adjacent compartments, or by circular walls to form inner and outer annular compartments.

The wells can be designed such that a single well includes a single cell. An individual cell may also be isolated in any other suitable container, e.g., microfluidic chamber, droplet, nanowell, tube, etc.—Any convenient method for manipulating single cells may be employed, where such methods include fluorescence activated cell sorting (FACS), robotic device injection, gravity flow, or micromanipulation and the use of semi-automated cell pickers (e.g. the Quixell™ cell transfer system from Stoelting Co.), etc. In some instances, single cells can be deposited in wells of a plate according to Poisson statistics (e.g., such that approximately 10%, 20%, 30% or 40% or more of the wells contain a single cell—which number can be defined by adjusting the number of cells in a given unit volume of fluid that is to be dispensed into the containers). In some instances, a suitable reaction vessel comprises a droplet (e.g., a microdroplet). Individual cells can, for example, be individually selected based on features detectable by microscopic observation, such as location, morphology, reporter gene expression, antibody labelling, FISH, intracellular RNA labelling, or qPCR.

Following obtainment of single cells, e.g., as described above, mRNA can be released from the cells by lysing the cells. Lysis can be achieved by, for example, heating or freeze-thaw of the cells, or by the use of detergents or other chemical methods, or by a combination of these. However, any suitable lysis method can be used. A mild lysis procedure can advantageously be used to prevent the release of nuclear chromatin, thereby avoiding genomic contamination of the cDNA library, and to minimize degradation of mRNA. For example, heating the cells at 72° C. for 2 minutes in the presence of Tween-20 is sufficient to lyse the cells while resulting in no detectable genomic contamination from nuclear chromatin. Alternatively, cells can be heated to 65° C. for 10 minutes in water (Esumi et al., Neurosci Res 60(4):439-51 (2008)); or 70° C. for 90 seconds in PCR buffer II (Applied Biosystems) supplemented with 0.5% NP-40 (Kurimoto et al., Nucleic Acids Res 34(5):e42 (2006)); or lysis can be achieved with a protease such as Proteinase K or by the use of chaotropic salts such as guanidine isothiocyanate (U.S. Publication No. 2007/0281313).

Synthesis of cDNA from template nucleic acid mRNA in the methods described herein can be performed directly on cell lysates, such that a reaction mix for reverse transcription is added directly to cell lysates. Alternatively, mRNA can be purified after its release from cells. This can help to reduce mitochondrial and ribosomal contamination. mRNA purification can be achieved by any method known in the art, for example, by binding the mRNA to a solid phase. Commonly used purification methods include paramagnetic beads (e.g. Dynabeads). Alternatively, specific contaminants, such as ribosomal RNA can be selectively removed using affinity purification.

Where desired, a given single cell workflow may include a pooling step where a cDNA product composition, e.g., made up of synthesized first strand cDNAs or synthesized double stranded cDNAs, is combined or pooled with the cDNA product compositions obtained from one or more additional cells. The number of different cDNA product compositions produced from different cells that are combined or pooled in such embodiments may vary, where the number ranges in some instances from 2 to 50, such as 3 to 25, including 4 to 20 or 10,000, or more. Prior to or after pooling, the product cDNA composition(s) can be amplified, e.g., by polymerase chain reaction (PCR), such as described above.

In some instances, emulsion PCR may be employed. For emulsion PCR, an emulsion PCR reaction (e.g., in a droplet, droplet microreactor) is created with a "water in oil" mix to generate thousands or millions of micron-sized aqueous compartments. Sources of nucleic acids (e.g., cells, nucleic acid libraries, optionally coupled to solid supports, e.g., beads) are mixed in a limiting dilution prior to emulsification or directly into the emulsion mix. The combination of compartment size and limiting dilution nucleic acid sources is used to generate compartments containing, on average, just one source of nucleic acid (e.g., cell, nucleic acid(s) stably associated with a solid support (e.g., bead) etc.). Depending on the size of the aqueous compartments generated during the emulsification step, up to $3 \times 10^9$ individual amplification reactions per µl can be conducted simultaneously in the same container, e.g., tube, well or other suitable container. The average size of a compartment in an emulsion ranges from sub-micron in diameter to over a 100 microns, depending on the emulsification conditions.

As indicated above, in protocols that include a pooling step, the pooling step can be performed after or before amplification of a cDNA composition produced from a single cell. As such, in certain embodiments of the methods described herein, cells are obtained from a tissue of interest and a single-cell suspension is obtained. A single cell is placed in one well of a multi-well plate, or other suitable container, such as a microfluidic chamber or tube. The cells are lysed and reverse transcription reaction mix is added directly to the lysates without additional purification. It is also possible that the container vessel also contains reverse transcription reagents when the cells are lysed. This results in the synthesis of cDNA from cellular mRNA and incorporation of a source (e.g., cell) barcode tag into the cDNA, e.g., as described above. The tagged cDNA samples are amplified and pooled, and then sequenced to produce reads. In yet other embodiments, cells are obtained from a tissue of interest and a single-cell suspension is obtained. A single cell is placed in one well of a multi-well plate or other suitable container. The cells are lysed and reverse transcription reaction mix is added directly to the lysates without additional purification. This results in the synthesis of cDNA from cellular mRNA and incorporation of a source barcode tag into the cDNA. The tagged cDNA samples are pooled and amplified and then sequenced to produce reads. This allows identification of genes that are expressed in each single cell. The NGS libraries produced according to the methods of the present disclosure may exhibit a desired complexity (e.g., high complexity). The "complexity" of a NGS library relates to the proportion of redundant sequencing reads (e.g., sharing identical start sites) obtained upon sequencing the library. Complexity is inversely related to the proportion of redundant sequencing reads. In a low complexity library, certain target sequences are over-represented, while other targets (e.g., mRNAs expressed at low levels) suffer from little or no coverage. In a high complexity library, the sequencing reads more closely track the known distribution of target nucleic acids in the starting nucleic acid sample, and will include coverage, e.g., for targets known to be present at relatively low levels in the starting sample (e.g., mRNAs expressed at low levels). According to certain embodiments, the complexity of a NGS library produced according to the methods of the present disclosure is such that sequencing reads are produced for 70% or more, 75% or more, 80% or more, 85% or more, 90% or more, 95% or more, 96% or more, 97% or more, 98% or more, or 99% or more of the different species of target nucleic acids (e.g., different species of mRNAs) in the starting nucleic acid sample (e.g., RNA sample). The complexity of a library may be determined by mapping the sequencing reads to a reference genome or transcriptome (e.g., for a particular cell type). Specific approaches for determining the complexity of sequencing libraries have been developed, including the approach described in Daley et al. (2013) *Nature Methods* 10(4):325-327.

In certain aspects, the methods of the present disclosure further include subjecting the NGS library to a NGS protocol. The protocol may be carried out on any suitable NGS sequencing platform. NGS sequencing platforms of interest include, but are not limited to, a sequencing platform provided by Illumina® (e.g., the HiSeq™, MiSeq™ and/or NextSeq™ sequencing systems); Ion Torrent™ (e.g., the Ion PGM™ and/or Ion Proton™ sequencing systems); Pacific Biosciences (e.g., the PACBIO RS II Sequel sequencing system); Life Technologies™ (e.g., a SOLiD sequencing system); Roche (e.g., the 454 GS FLX+ and/or GS Junior sequencing systems); or any other sequencing platform of interest. The NGS protocol will vary depending on the particular NGS sequencing system employed. Detailed protocols for sequencing an NGS library, e.g., which may include further amplification (e.g., solid-phase amplification), sequencing the amplicons, and analyzing the sequencing data are available from the manufacturer of the NGS sequencing system employed.

In certain embodiments, the subject methods may be used to generate a NGS library corresponding to mRNAs for downstream sequencing on a sequencing platform of interest (e.g., a sequencing platform provided by Illumina®, Ion Torrent™, Pacific Biosciences, Life Technologies™, Roche, or the like). According to certain embodiments, the subject methods may be used to generate a NGS library corresponding to non-polyadenylated RNAs for downstream sequencing on a sequencing platform of interest. For example, microRNAs may be polyadenylated and then used as templates in a template switch polymerization reaction as described elsewhere herein. Random or gene-specific priming may also be used, depending on the goal of the researcher. The library may be mixed 50:50 with a control library (e.g., Illumina®'s PhiX control library) and sequenced on the sequencing platform (e.g., an Illumina® sequencing system). The control library sequences may be removed and the remaining sequences mapped to the transcriptome of the source of the mRNAs (e.g., human, mouse, or any other mRNA source).

Compositions

Also provided by the present disclosure are compositions. Compositions of embodiments of the invention may include, e.g., one or more of any of the reaction mixture components described above with respect to the subject methods. For example, the compositions may include one or more of a RNA (e.g., a control RNA), a polymerase (e.g., a polymerase capable of template-switching, a thermostable polymerase, combinations thereof, or the like), a first-strand cDNA primer having any of the domains described above, a template switch oligonucleotide having any of the domains described above, dNTPs, a salt, a metal cofactor, one or more nuclease inhibitors (e.g., an RNase inhibitor), one or more enzyme-stabilizing components (e.g., DTT), one or more transposome complexes (e.g., containing a first and/or second post-tagmentation amplification binding site) or any other desired reaction mixture component(s).

In certain aspects, the subject compositions include a template mRNA and a template switch oligonucleotide each hybridized to adjacent regions of a first strand cDNA, where the first strand cDNA includes: (a) a first post-tagmentation amplification, e.g., PCR, primer binding domain and a first cDNA amplification, e.g., PCR, primer domain 5' of an oligo dT domain; and (b) a second pre-tagmentation amplification, e.g., PCR, primer binding domain at the 3' end of the first strand cDNA. In certain aspects, the first and second pre-tagmentation amplification, e.g., PCR, primer binding domains are complementary. According to certain embodiments, the first strand cDNA further includes a source barcode (e.g., cell barcode) domain 5' of the oligo dT domain. Also provided are compositions that include a double stranded cDNA produced from the above-described composition, e.g., produced by amplification, such as PCR amplification, of the first strand cDNA.

In certain aspects, provided is a tagmented sample produced by tagmenting the above-described double stranded cDNA. The tagmenting may be performed with one or more transposomes including a transposase and a transposon nucleic acid that includes a transposon end domain and a second post-tagmentation amplification, e.g., PCR, primer binding domain, to produce a tagmented sample.

Also provided is a NGS library produced by amplification (e.g., PCR amplification) of the above-described tagmented sample. The NGS library may include a plurality of doubled stranded NGS-ready deoxyribonucleic acids (DNAs) that each includes terminal sequencing platform adapter constructs, e.g., as described above. The sequencing platform adapter constructs may include adapter sequences, indexing sequences, source barcode sequences, unique molecular identification sequences, etc., as desired.

The subject compositions may be present in any suitable environment. According to one embodiment, the composition is present in a reaction tube (e.g., a 0.2 mL tube, a 0.6 mL tube, a 1.5 mL tube, or the like) or a well or microfluidic chamber or droplet or other suitable container. In certain aspects, the composition is present in two or more (e.g., a plurality of) reaction tubes or wells (e.g., a plate, such as a 96-well plate, a multi-well plate, e.g., containing about 1000, 5000, or 10,000 or more wells). The tubes and/or plates may be made of any suitable material, e.g., polypropylene, or the like, PDMS, or aluminium. The containers may also be treated to reduce adsorption of nucleic acids to the walls of the container. In certain aspects, the tubes and/or plates in which the composition is present provide for efficient heat transfer to the composition (e.g., when placed in a heat block, water bath, thermocycler, and/or the like), so that the temperature of the composition may be altered within a short period of time, e.g., as necessary for a particular enzymatic reaction to occur. According to certain embodiments, the composition is present in a thin-walled polypropylene tube, or a plate having thin-walled polypropylene wells or materials such as aluminium having high heat conductance. In some instances, the compositions of the disclosure may be present in droplets. In certain embodiments it may be convenient for the reaction to take place on a solid surface or a bead, in such case, the first strand cDNA primer and/or template switch oligonucleotide, or one or more other primers, may be attached to the solid support or bead by methods known in the art—such as biotin linkage or by covalent linkage—and reaction allowed to proceed on the support. Alternatively, the oligos may be synthesized directly on the solid support—e.g. as described in Macosko, E Z et. al, Cell 161, 1202-1214, May 21, 2015).

Other suitable environments for the subject compositions include, e.g., a microfluidic chip (e.g., a "lab-on-a-chip device", e.g., a microfluidic device comprising channels and inlets). The composition may be present in an instrument configured to bring the composition to a desired temperature, e.g., a temperature-controlled water bath, heat block, heat block adaptor, or the like. The instrument configured to bring the composition to a desired temperature may be configured to bring the composition to a series of different desired temperatures, each for a suitable period of time (e.g., the instrument may be a thermocycler).

Kits

Aspects of the present disclosure also include kits. The kits may include, e.g., one or more of any of the reaction mixture components described above with respect to the subject methods. For example, the kits may include: a first strand cDNA primer including a 3' oligo dT domain, a first post-tagmentation amplification primer binding domain and a 5' first pre-tagmentation amplification primer binding domain; and a template switch oligonucleotide including a 3' hybridization domain and a 5' second pre-tagmentation amplification primer binding domain, e.g., as described above. In yet other instances, the kits may include: a first strand cDNA primer including a 3' oligo dT domain and a 5' first pre-tagmentation amplification primer binding domain; and a template switch oligonucleotide including a 3' hybridization domain and a 5' second pre-tagmentation amplification primer binding domain flanking a first post-tagmentation amplification primer binding domain, e.g., as described above. In either of the above embodiment, the first and second pre-tagmentation amplification primer binding domains may be identical or different.

The kits may further include one or more transposome including a transposase and a transposon nucleic acid including a transposon end domain and a second post-tagmentation amplification primer binding domain, e.g., as described above. The kits may further include pre-tagmentation amplification primers, post-tagmentation amplification primers, etc. Any primers/oligonucleotides provided in the kits may include any of the domains/features described above in the section relating to the methods of the present disclosure.

The kits may further include one or more of a template ribonucleic acid (RNA), components for producing a template RNA from a precursor RNA (e.g., a poly(A) polymerase and associated reagents for polyadenylating a non-polyadenylated precursor RNA), a polymerase (e.g., a polymerase capable of template-switching, a thermostable polymerase, combinations thereof, or the like), dNTPs, a salt, a metal cofactor, one or more nuclease inhibitors (e.g., an RNase inhibitor and/or a DNase inhibitor), one or more molecular crowding agents (e.g., polyethylene glycol, or the like), one or more enzyme-stabilizing components (e.g., DTT), or any other desired kit component(s), such as solid supports, e.g., tubes, beads, microfluidic chips, etc.

In certain embodiments, the kits include reagents for isolating RNA from a source of RNA. The reagents may be suitable for isolating nucleic acid samples from a variety of RNA sources including single cells, cultured cells, tissues, organs, or organisms. The subject kits may include reagents for isolating a nucleic acid sample from a fixed cell, tissue or organ, e.g., formalin-fixed, paraffin-embedded (FFPE) tissue. Such kits may include one or more deparaffinization agents, one or more agents suitable to de-crosslink nucleic acids, and/or the like.

Components of the kits may be present in separate containers, or multiple components may be present in a single container. For example, the template switch oligonucleotide and the template switching polymerase may be provided in the same tube, or may be provided in different tubes. In certain embodiments, it may be convenient to provide the components in a lyophilized form, so that they are ready to use and can be stored conveniently at room temperature.

In addition to the above-mentioned components, a subject kits may further include instructions for using the components of the kit, e.g., to practice the subject method. The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, Hard Disk Drive (HDD), portable flash drive, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Utility

The subject methods find use in a variety of applications, including those that require the presence of particular nucleotide sequences at one or both ends of nucleic acids of interest. Such applications exist in the areas of basic research and diagnostics (e.g., clinical diagnostics) and include, but are not limited to, the generation of NGS libraries. Such libraries may include adapter sequences that enable sequencing of the library members using any convenient sequencing platform, including: the HiSeq™, MiSeq™ and NextSeq™ sequencing systems from Illumina®; the Ion PGM™ and Ion Proton™ sequencing systems from Ion Torrent™; the PACBIO RS II Sequel sequencing system from Pacific Biosciences, the SOLiD sequencing systems from Life Technologies™, the 454 GS FLX+ and GS Junior sequencing systems from Roche, or any other convenient sequencing platform. The methods of the present disclosure find use in generating NGS libraries corresponding to any RNA starting material of interest (e.g., mRNA) and are not limited to polyadenylated RNAs. For example, the subject methods may be used to generate NGS libraries from non-polyadenylated RNAs, including microRNAs, small RNAs, siRNAs, and/or any other type non-polyadenylated RNAs of interest. The methods also find use in generating strand-specific information, which can be helpful in determining allele-specific expression or in distinguishing overlapping transcripts in the genome.

An aspect of the subject methods is that—utilizing a template RNA—a cDNA species having sequencing platform adapter sequences at one or both of its ends is generated, e.g., without the added steps associated with traditional approaches for generating hybrid nucleic acid molecules for downstream sequencing applications, such as 5' ligation, washing steps, and any other necessary steps associated with traditional ligation-based approaches. Accordingly, the methods of the present disclosure are more efficient, cost-effective, and provide more flexibility than the traditional approaches.

The following examples are offered by way of illustration and not by way of limitation.

Experimental

I. Production and Analysis of Product Double Stranded cDNAs

Double stranded cDNA was produced according to the example strategy shown in FIG. 2, which involves the template-switching activity of reverse transcriptases to enrich for full-length cDNAs and to add defined PCR adapters directly to both ends of the first-strand cDNA. Non-templated nucleotides are added by the reverse transcriptase when it reaches the 5' end of the mRNA during cDNA synthesis. Template switching then occurs when a specially designed template-switching oligo (SMART-Seq v4 Oligonucleotide) that has a complementary sequence to these non-templated nucleotides hybridizes to the first-strand cDNA. The RT switches from using the mRNA as a template to using the new template for further cDNA synthesis. This ensures that the 5' end of the mRNA is captured and allows for downstream amplification and enrichment of full-length cDNA by LD PCR (Long Distance PCR). The SMART-Seq v4 Ultra Low Input RNA Kit for Sequencing improves upon this method by incorporating locked nucleic acid (LNA) modifications to the template switching oligo and ligation-inhibiting blocks on the priming oligonucleotides, as well as modifications that prevent the polymerase from switching from the template switch oligonucleotide to a different template nucleic acid after synthesizing the compliment of the 5' end of the template switch oligonucleotide (e.g., a 5' adapter sequence of the template switch oligonucleotide). Useful modifications include, but are not limited to, an abasic lesion (e.g., a tetrahydrofuran derivative), a nucleotide adduct, an iso-nucleotide base (e.g., isocytosine, isoguanine, and/or the like), and any combination thereof.

Figures 4A, 4B, 4C:
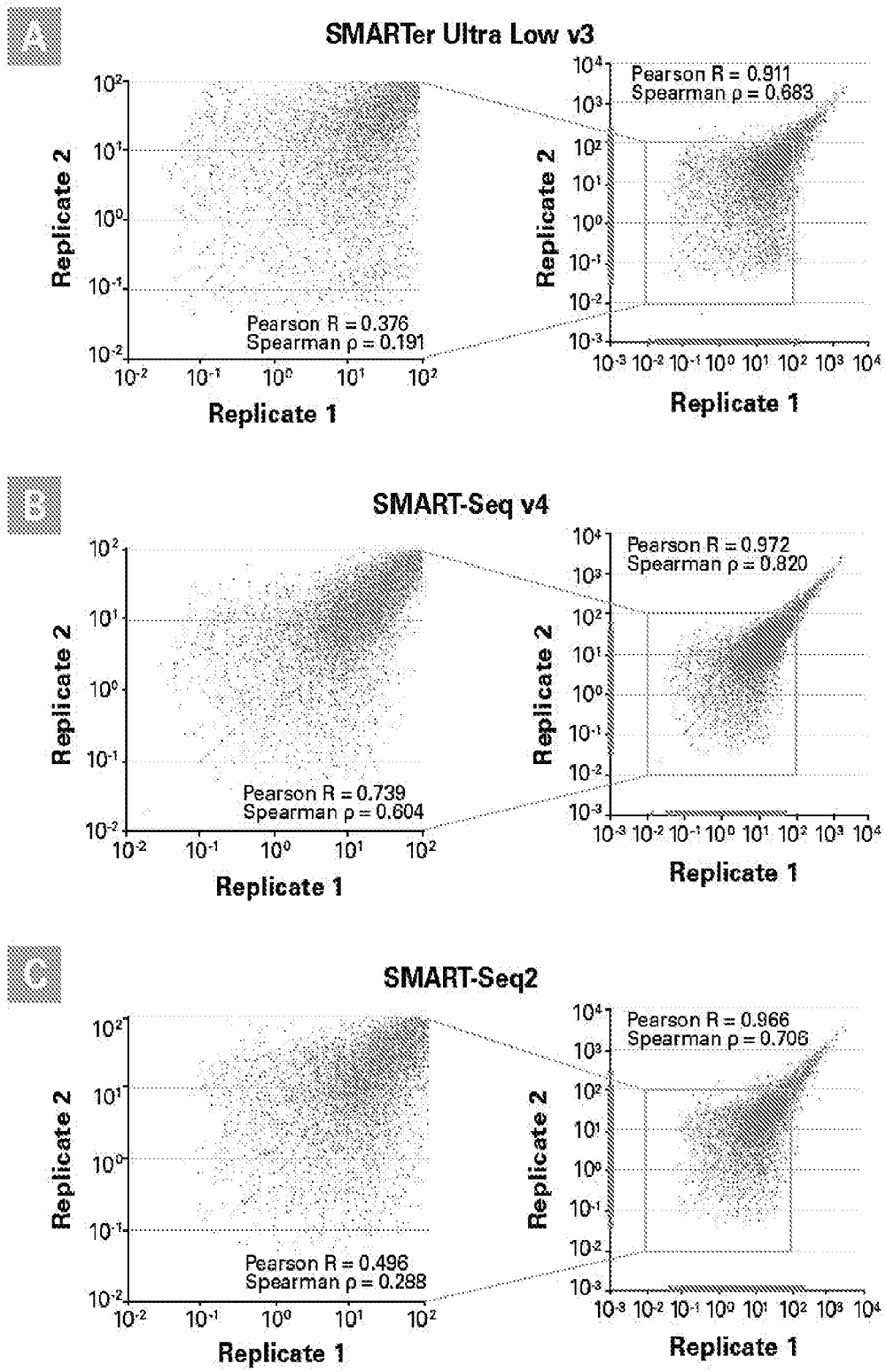
FIGS. 4A, 4B and 4C show FPKM (Fragments Per Kilobase of exon per Million reads) data upon sequencing product double stranded cDNAs produced according to the embodiment illustrated in FIG. 2.

FIGS. 4A to 4C show FPKM (Fragments Per Kilobase of exon per Million reads) data indicating that the SMART-Seq v4 kit improves reproducibility for low-input samples. FPKMs were compared for replicate libraries generated from 10 pg of mouse brain total RNA (Clontech) using the SMART-Seq v4 kit, the SMARTer® Ultra Low v3 kit, or the SMART-Seq2 method (Picelli et al., 2013). For all transcripts (shown in the scatter plots on the right) the correlation (Pearson R) between replicates was high for each of the three methods (R=0.911-0.972). The SMART-Seq v4 kit had the highest correlation (Panel B, right; R=0.972). Transcripts represented in only one replicate can be seen along the x- and y-axes of the scatter plots showing all transcripts (right sides of panels); the SMART-Seq v4 kit had less dropout (genes identified in one replicate, but not the other), and these dropouts had lower FPKM values than in the other protocols. For transcripts with FPKM<100 (lower expression), the correlation between replicates was much higher for the SMARTSeq v4 kit (Panel B, left; R=0.739) compared to the SMARTer Ultra Low v3 kit (Panel A, left; R=0.376) or the SMART-Seq2 method (Panel C, left; R=0.496). This data demonstrates that the methods described herein are highly reproducible for low-input samples.

II. NGS Library for Differential Expression

Described herein is a method to capture the 3' or 5' end of mRNA, convert it to cDNA, and add adapters specific for next generation sequencing (e.g., Illumina read primers and cluster generation sequences). In this example, cDNA is synthesized by priming with an adapter sequence that includes an oligo dT stretch, designed to prime the reverse transcriptase at the polyA tail. In this way, every mRNA will only have one initiation site, allowing for more accurate quantification of transcript levels.

Experiments were performed in which full-length cDNA was amplified using a template switching oligonucleotide containing an LNA modification in the backbone combined with a blocked oligo strategy, to prevent secondary template switching. These experiments added the same sequence on both ends of the cDNA during synthesis (added to the oligo dT and template switch primers). Complex libraries having high yields after cDNA amplification and high levels of transcripts identified were produced.

For the end-capture workflow, experiments were performed in which full-length cDNA was amplified using the same sequence as in the SMART oligo (IIA) (i.e., pre-tagmentation amplification primer binding site) from the full-length experiments on the template switching oligonucleotide, but still adding the Illumina adapter on the oligo dT primer. The complexity was higher than in the sheared RNA experiments, but not as high as when the adapter was the same on both ends. In addition, the distribution of the cDNA was shifted toward lower molecular weight molecules.

An experiment was designed to compare different priming oligos. All experiments involved template switching to the LNA oligo with the IIA adapter sequence. The three priming oligos all contained dT30, but they either had: (1) IIA sequence alone, (2) RP2 (Illumina) sequence alone; or (3) the IIA and RP2 sequences—where the IIA sequence was 5' to the RP2 sequence. Scenario (1) was identical to the "full length" experiments performed previously, and was used as a control for the highest complexity libraries from single cell equivalent inputs (10 pg total RNA). The cDNA was amplified by 17 cycles of cDNA amplification PCR using the IIA sequence. Scenario (2) was similar to previous attempts, and resulted in lower complexity libraries, with distributions shifted towards lower molecular weights. The cDNA was amplified using both the IIA sequence and the RP2 sequence. The presence of the RP2 permits selection for the 3' end of the original mRNA in subsequent reactions. Data was assessed as to whether distributions and yields similar to Scenario 1 were achieved with the oligo for Scenario 3. In this experiment, amplifying was only performed with the IIA sequence, but the presence of the RP2 sequence would allow for selection of the 3' end (similar to scenario 2). Yield and distribution were used as tests.

After performing the RT and PCR reactions as described above, it was found that the distribution for scenario (1) had a peak at ~2500 bp and a yield of 608 pg/µl. Scenario (2) had a peak of ~2000 bp and a yield of 335 pg/µl, while scenario (3) had a peak at ~2500 bp and a yield of 548 pg/µl. NRC (no RNA control) experiments were performed in parallel. Yields from those reactions were negligible.

Subsequent experiments continued to employ the CDS having the both the RP2 and IIA sequence. It was found that the IIA sequence did increase complexity of the library, although not to the same level that was found with the oligonucleotides lacking the RP2 sequence. We also found that the presence of the RP2 sequence did allow for selectivity of the 3' end.

The additional Illumina sequences were added through tagmentation and selective PCR—adding a sequencing primer to the 5' end of the captured sequence through tagmentation and cluster generation and indexing sequences through PCR.

Library Preparation and Analysis

A NGS library was prepared according to the end-capture method schematically illustrated in FIG. 3A. Briefly, cDNA is synthesized with a blocked and modified oligo(dT) primer that adds sequences for subsequent amplification and analysis: a cell barcode; part of the Illumina read primer 2 sequence that is used during library amplification; and the SMART IIA sequence that is used during cDNA amplification. The reverse transcriptase (in this example SMART-Scribe™ reverse transcriptase) copies the template into first strand cDNA by extending from the oligo dT primer. Upon reaching the the 5' end of the template RNA, it switches from the mRNA to the SMART-Seq v4 Oligonucleotide. After reverse transcription, the full-length cDNA is amplified by PCR with blocked Primer IIA oligonucleotides. After PCR, the presence of the barcode allows for pooling of the samples (in this case 12 samples were used, but can adjusted as necessary). The pooled samples are tagmented—Illumina Nextera® read primer 1 and 2 sequences are added by the Nextera® Tn5 transposon (TnRP1 and TnRP2). The 3' ends of the original cDNA are captured by selective PCR with primers for the TnRP1 and RP2 sequences. In this example, other products of the transposon-based reaction are not amplified, either because they lack all the necessary primer sites for amplification or because of suppression PCR. Cluster generation and indexing sequences are added during the library amplification PCR stage to generate a library ready for sequencing on an Illumina platform (e.g., as illustrated FIG. 3C).

Figures 5, 6:
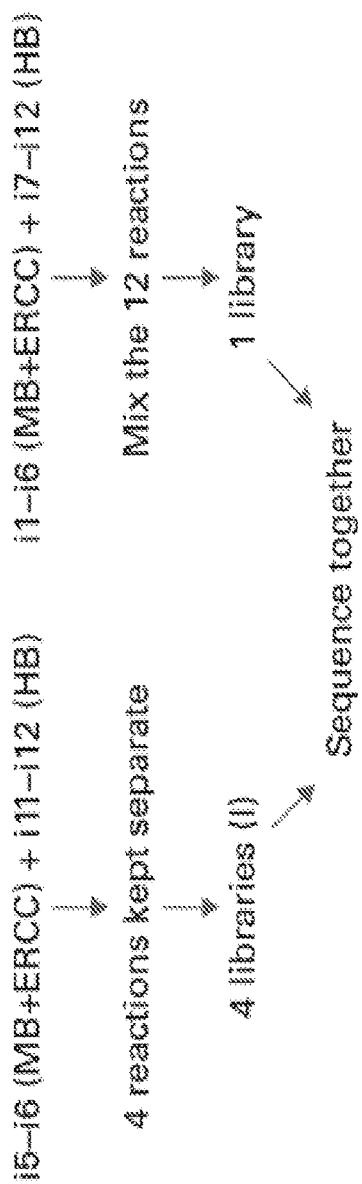
FIG. 5 is a flow diagram of an experiment designed to test the NGS library preparation method illustrated in FIG. 3A.
FIG. 6 provides mapping statistics for the libraries produced according to the experimental design shown in FIG. 5.

A flow diagram showing the experimental design for testing the NGS library produced according to the above-described end-capture method is shown in FIG. 5. To test the validity of the pooling strategy, the experiment compared sequencing results from unpooled and pooled libraries. In this experiment, a total of 16 reactions were performed. Four unpooled reactions were performed: two reactions used mouse brain (MB) RNA (Clontech) with External RNA Control Consortium (ERCC) spike-in controls (Thermo Fisher Scientific) and priming oligos containing cell barcodes labeled index5 (i5) or index6 (i6); and two reactions used human brain (HB) RNA (Clontech) (without spike-in controls) and priming oligos containing cell barcodes labeled index11 (i11) and index12 (i12). These samples were kept un-pooled until they were loaded on the sequencer to run. An additional twelve reactions were performed using twelve priming oligos with cell barcodes labeled indexes (i1-i12). Of these twelve reactions, six used mouse brain (MB) RNA with ERCC spike-in controls (i1-i6), while six were made using human brain (HB) RNA (i7-i12). These reactions were pooled after PCR (according to the method outlined in FIG. 3A), and a single Illumina index was added to the pooled samples. The five libraries (four unpooled and one pooled) were multiplexed and sequenced together on an Illumina MiSeq® sequencing system. The results of the above-described experiment are shown in FIGS. 6-9; the four unpooled libraries are labeled independent (I).

Mapping statistics for the pooled and unpooled libraries are shown in FIG. 6. The five libraries (four unpooled and one pooled) were sequenced on an Illumina MiSeq® instrument with 150 bp for read 1 and 30 bp for read 2. The pooled libraries were de-multiplexed based on the cell barcode sequence from read 2. All libraries were mapped with TopHat v2.0.9/Bowtie2 v2.1.0 against the mouse genome (mm10) or human genome (hg19). The four unpooled libraries are independently labeled (I). In the case of the pooled samples, the reads map to the genome at a high rate (74-89%) with a small proportion mapping to rRNA or mitochondrial regions. There were no obvious differences between the libraries within or not within the pooled sample. The proportion of reads that map to the ERCC transcripts was also measured. The ERCC spike-in controls were added only to the mouse brain-derived libraries and these libraries contain reads that map to the ERCC transcripts. In the unpooled libraries, no ERCC reads were detected in the two human brain-derived libraries; however, a small percentage of the reads from the human brain libraries that were pooled mapped to the ERCC transcripts (<0.02%).

Figure 7A:
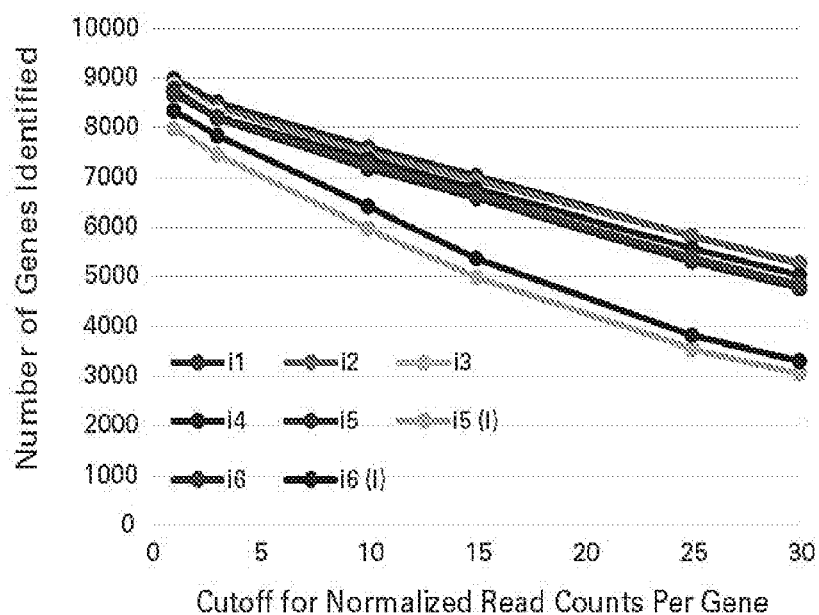
FIGS. 7A and 7B show graphs indicating normalized read counts per gene as determined by DESeq2 analysis of mapped libraries.
Figure 7B:
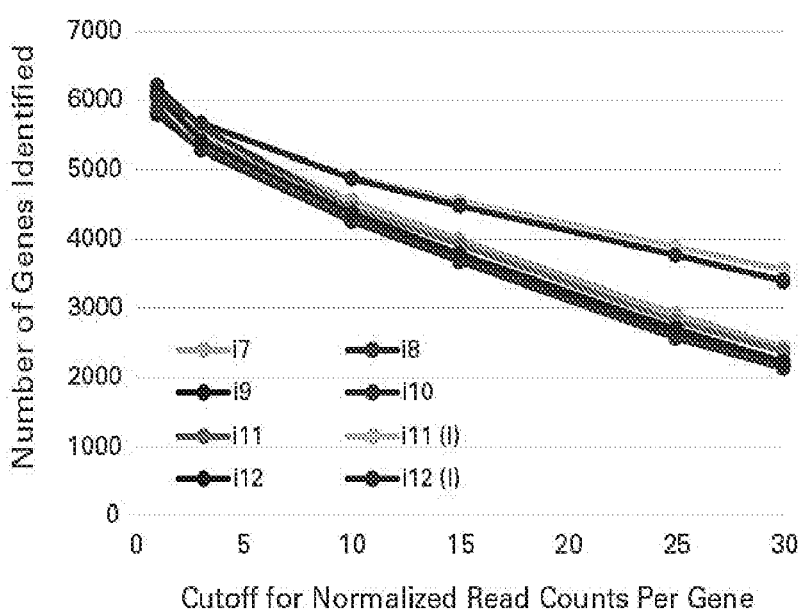

FIGS. 7A and 7B show graphs indicating normalized read counts per gene as determined by DESeq2 v1.8.1 analysis of mapped libraries. The number of genes identified with different cutoffs (1, 3, 10, 15, 25, and 30) for normalized read counts are plotted. The data indicates that the present approach enables the identification of a large number of genes from both the pooled and independent samples.

Figures 8A, 8B:
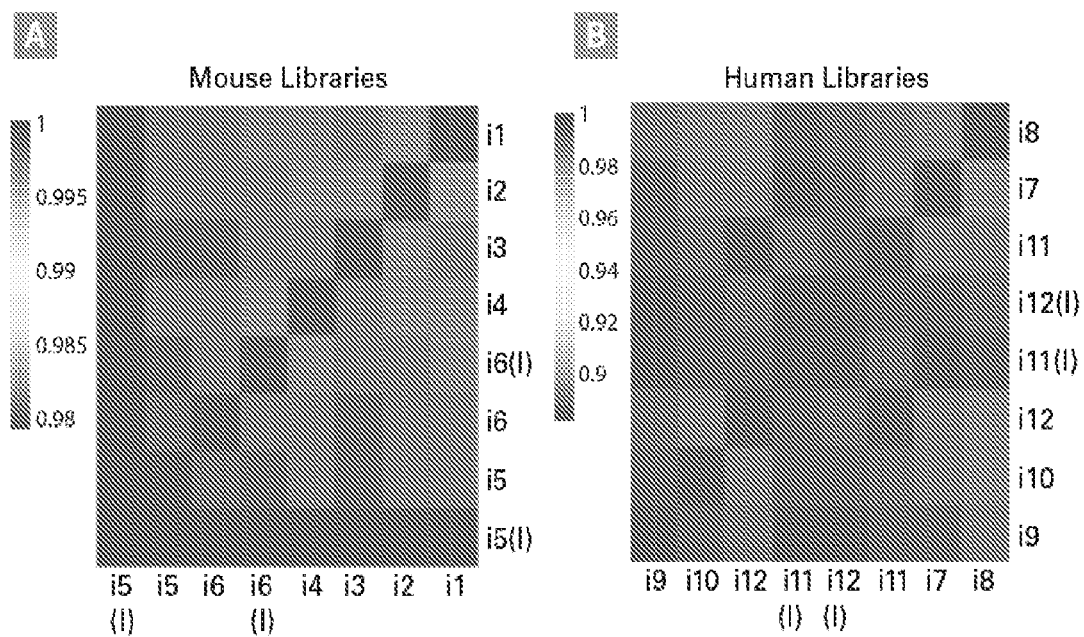
FIGS. 8A and 8B show heat maps representing the Pearson correlations of regularized log-transformed readcounts (rlog) for libraries derived from mouse brain samples (FIG. 8A) and human brain samples (FIG. 8B).

FIGS. 8A and 8B show heat maps representing the Pearson correlations of regularized log-transformed read-counts (rlog) for libraries derived from mouse brain samples (FIG. 8A) and human brain samples (FIG. 8B). For all comparisons, the correlation (R) was >0.9. Overall, there is no evidence of a correlation bias, indicating that the unpooled samples (I) are not more similar to each other than the pooled samples and vice versa. The data indicates that the libraries are highly correlated regardless of pooling.

Figures 9A, 9B:
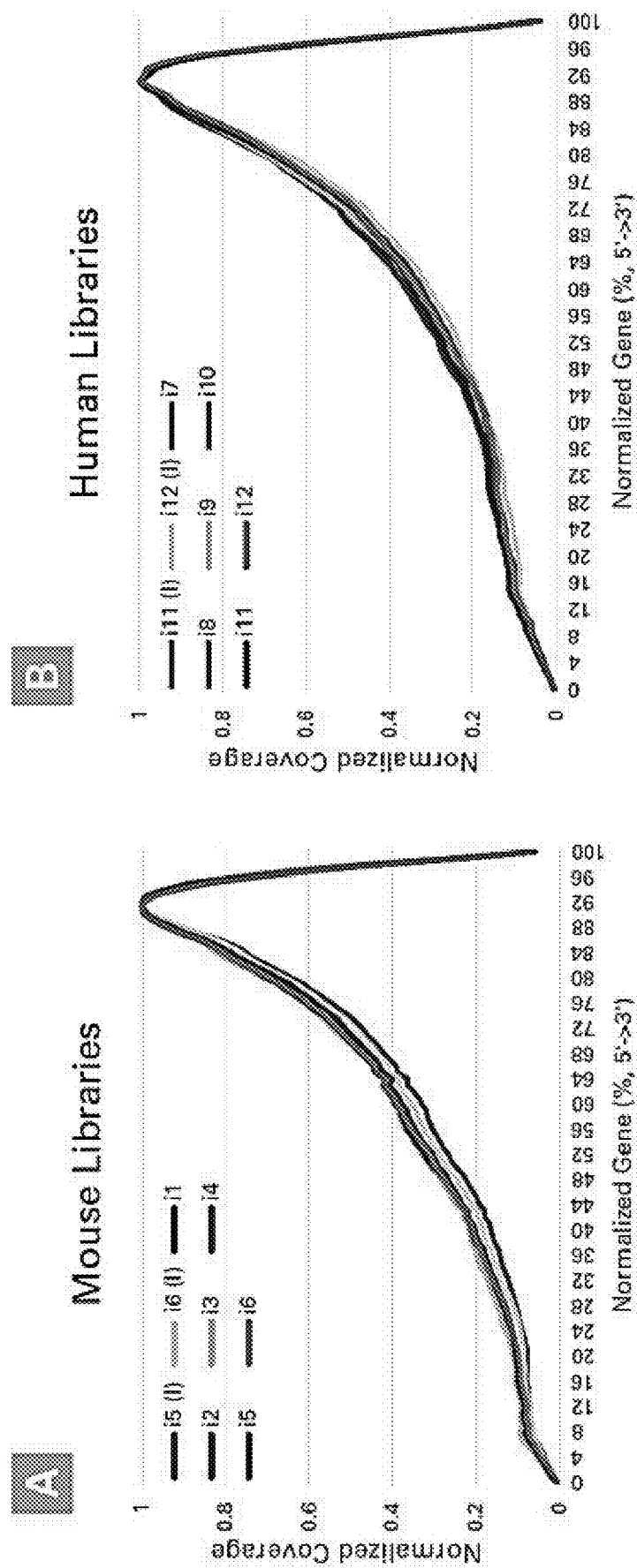
FIGS. 9A and 9B show graphs for gene body coverage analysis for unpooled and pooled libraries.

FIGS. 9A and 9B show gene body coverage analysis for unpooled and pooled libraries. Once the reads from each library were mapped to the mouse genome (FIG. 9A) or the human genome (FIG. 9B), gene body coverage analysis was performed to assess the ability of the methods to capture the 3' ends of the cDNA. Across all transcripts (normalized in length to 100%), the majority of reads mapped to the last 20% of the transcripts. There was no difference in 3' coverage between the pooled and unpooled methods, illustrating the accuracy of the selectivity of the second PCR reaction. The four unpooled libraries are labeled independent (I). The data indicates that the present approach enables efficient capture of 3' cDNA ends.

III. Single Transposome Mediated NGS Library Preparation

The embodiment illustrated in FIG. 3A utilize transposon complexes which are present with two different adapter sequences, labelled TnRP1 and TnRP2. Through selective PCR, the final amplified library contains only the TnRP1 sequence. In some embodiments, the method can be performed with using a transposome with only one adapter present, illustrated in FIG. 3D.

In this embodiment, cDNA is synthesized with a blocked and modified oligo(dT) primer that adds sequences for subsequent amplification and analysis: a cell barcode; part of the Illumina read primer 2 sequence that is used during library amplification; and the SMART IIA sequence that is used during cDNA amplification. The reverse transcriptase (in this example SMARTScribe™ reverse transcriptase) copies the template into first strand cDNA by extending from the oligo dT primer. Upon reaching the 5' end of the template RNA, it switches from the mRNA to the SMART-Seq v4 Oligonucleotide. After reverse transcription, the full-length cDNA is amplified by PCR with blocked Primer IIA oligonucleotides. After PCR, the presence of the barcode allows for pooling of the samples (in this case 12 samples were used but can be adjusted as necessary).

The pooled samples are tagmented—Illumina read primer 1 sequence is added by the Tn5 transposon (TnRP1). The 3' ends of the original cDNA are captured by selective PCR with primers for the TnRP1 and RP2 sequences. In this example, other products of the transposon-based reaction are not amplified, either because they lack all the necessary primer sites for amplification or because of suppression PCR. Cluster generation and indexing sequences are added during the library amplification PCR stage to generate a library ready for sequencing on an Illumina platform (e.g., illustrated in FIG. 3C).

A. Pooled cDNA and Library Profile

Figure 10A:
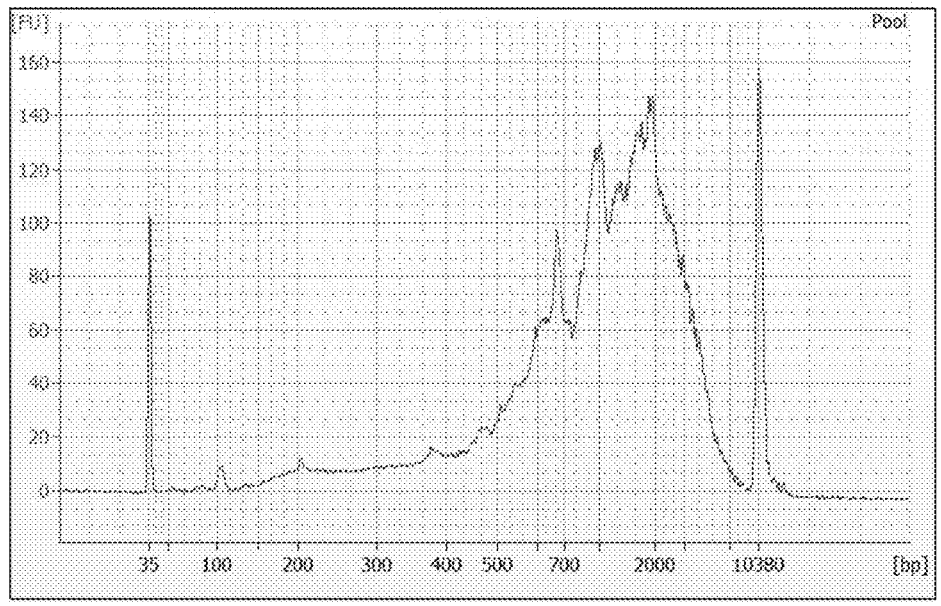
Figure 10A:
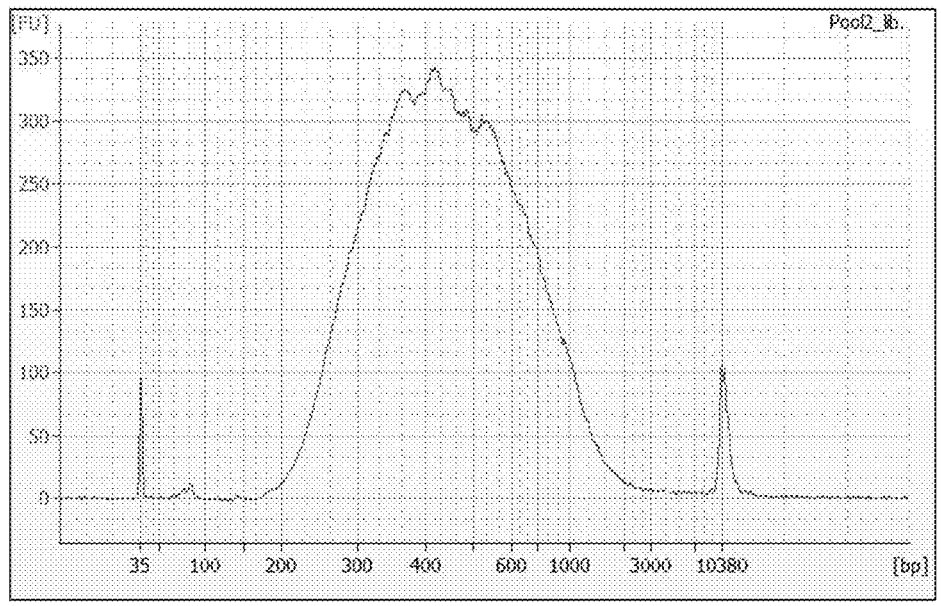
Figure 10C:
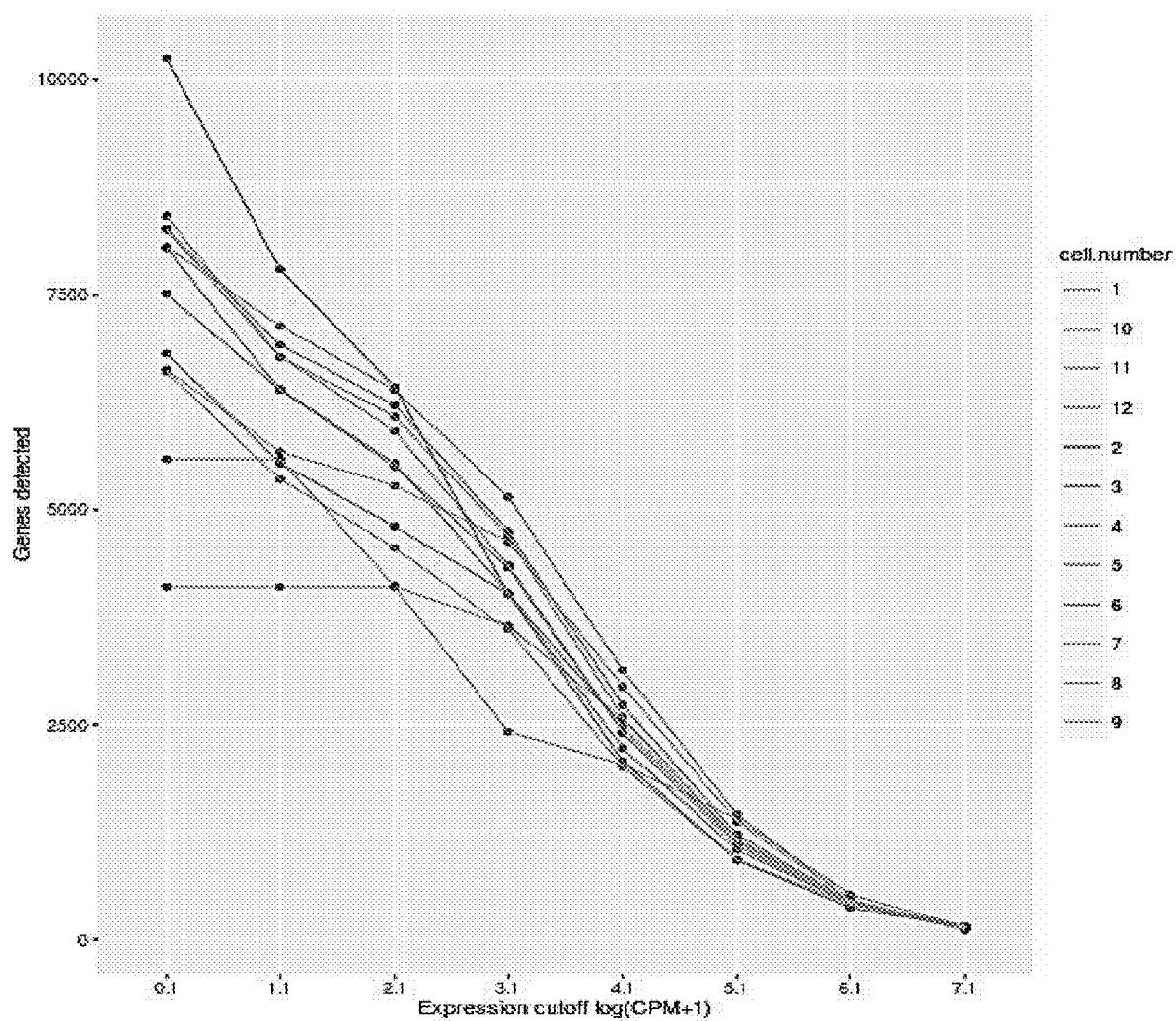

In this example, single cells were used for each reaction during cDNA synthesis and amplification. Additionally, a single transposome was used during the tagmentation reaction, illustrating the embodiment described above. To isolate single cells, K562 cells were diluted to one cell/μl in PBS buffer and 1 μl was spotted on a 96-well flat bottom plate. Each spot was inspected via optical microscopy to confirm single cells were present until twelve single cells were isolated, lysed, and subjected to cDNA synthesis according to the protocol illustrated in FIG. 3D. The cDNAs were generated with different barcodes on the first strand cDNA primer and could therefore be pooled and purified together. The full length cDNA was analyzed for size and concentration (see FIG. 10A cDNA panel). 2 ng of the purified cDNA was used for library preparation with a single transposome. The library was amplified with primers complementary to the Illumina read primer 2 sequence on the cDNA priming oligonucleotide and the TnRP1 sequence introduced during tagmentation. The resultant library was run on a Bioanalyzer and analyzed for yield and size distribution. FIG. 10A Library panel, shows that the size distribution is appropriate for Illumina sequencing, with a peak at 500 bp, and an overall distribution between 200 and 1500 bps. The overall yield is sufficient for sequencing, with a concentration in excess of 4 nM. This library was sequenced on an Illumina MiSeq with 47 cycles for read 1 and 26 cycles for read2. The data provided in FIG. 10B and FIG. 10C are generated from the analysis from this sequencing run.

B. Gene Body Coverage Analysis.

FIG. 10B shows gene body coverage analysis for the single cell libraries. Once the reads from each library were mapped to the human genome, gene body coverage analysis was performed to assess the ability of the methods to capture the 3' ends of the cDNA. Across all transcripts (normalized in length to 100%), the majority of reads mapped to the last 20% of the transcripts. The data indicates that the present approach with a single transposome enables efficient capture of 3' cDNA ends.

C. Number of Genes Identified From K562 Single Cells.

Mapped libraries were analyzed with CPM generated from STAR v.2.3.0.1 (Dobin et al. 2013 (Bioinformatics. 2013 Jan. 1; 29(1):15-21. STAR: ultrafast universal RNA-seq aligner. Dobin A, Davis C A, Schlesinger F, Drenkow J, Zaleski C, Jha S, Batut P, Chaisson M, Gingeras T R)). The number of genes identified with different cutoffs (0.1, 1.1, 2.1, 3.1, 4.1, 5.1, 6.1, and 7.1) for log-transformed CPM+1 were plotted, as illustrated in FIG. 10C. The amount of cDNA produced from each cell varies, leading to different read depths per cell. This affects the number of genes identified, as seen most easily for sample 10 at lower expression cutoff values. Even with different read depths across cells, the data indicates that the present approach enables the identification of a large number of genes from single cell samples.

D. Pearson Correlation Heat Map Matrix of K562 Single Cells.

Figure 10D:
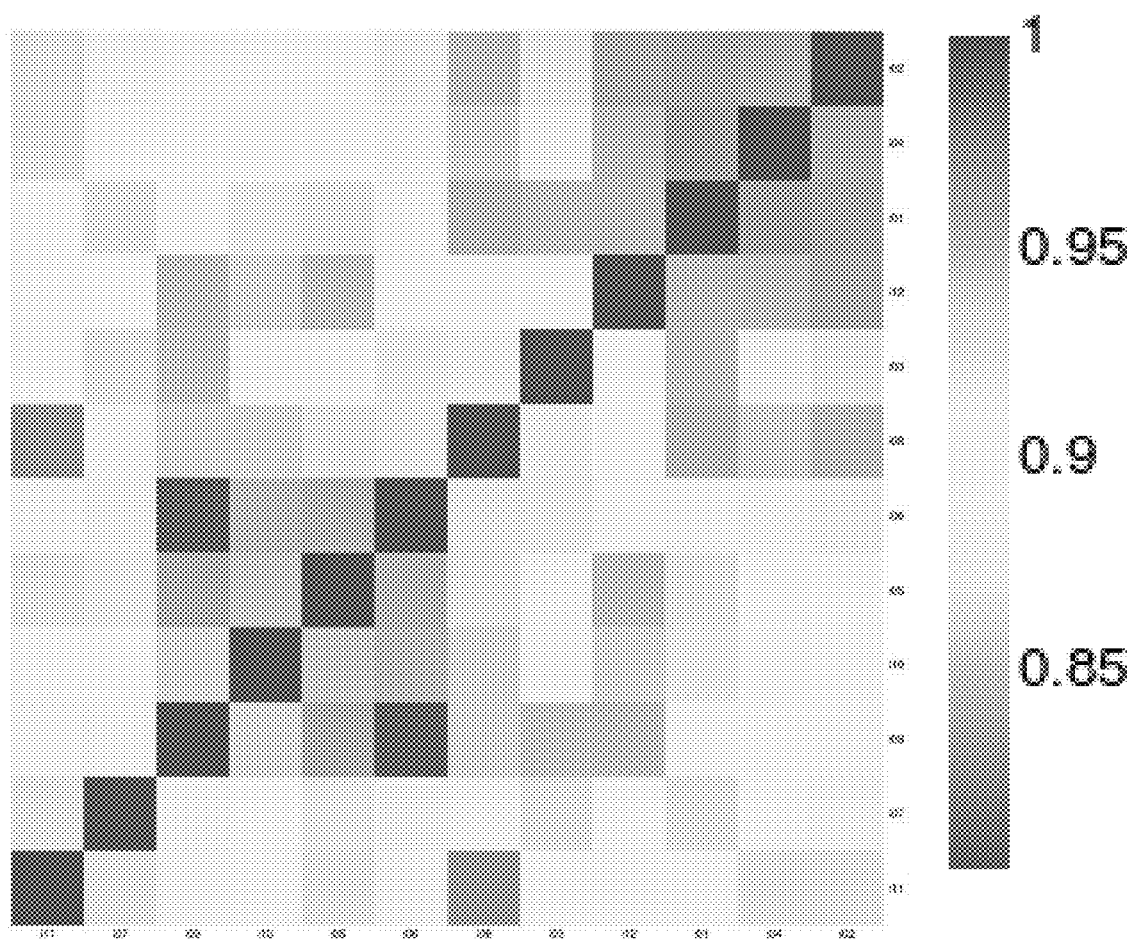

The heat map illustrated in FIG. 10D represents the Pearson correlations of expression levels for the 12 single-cell libraries. FIG. 10D shows heat maps representing the Pearson correlations of regularized log-transformed CPM+1 for libraries derived from the K562 single cells. For all comparisons, the correlation (R) was >0.7, while the majority of single-cell libraries are highly correlated (>0.9). The data indicates that the libraries are highly correlated.

IV. Effect of UMI on Oligo dT Primers

Figures 11A, 11B:
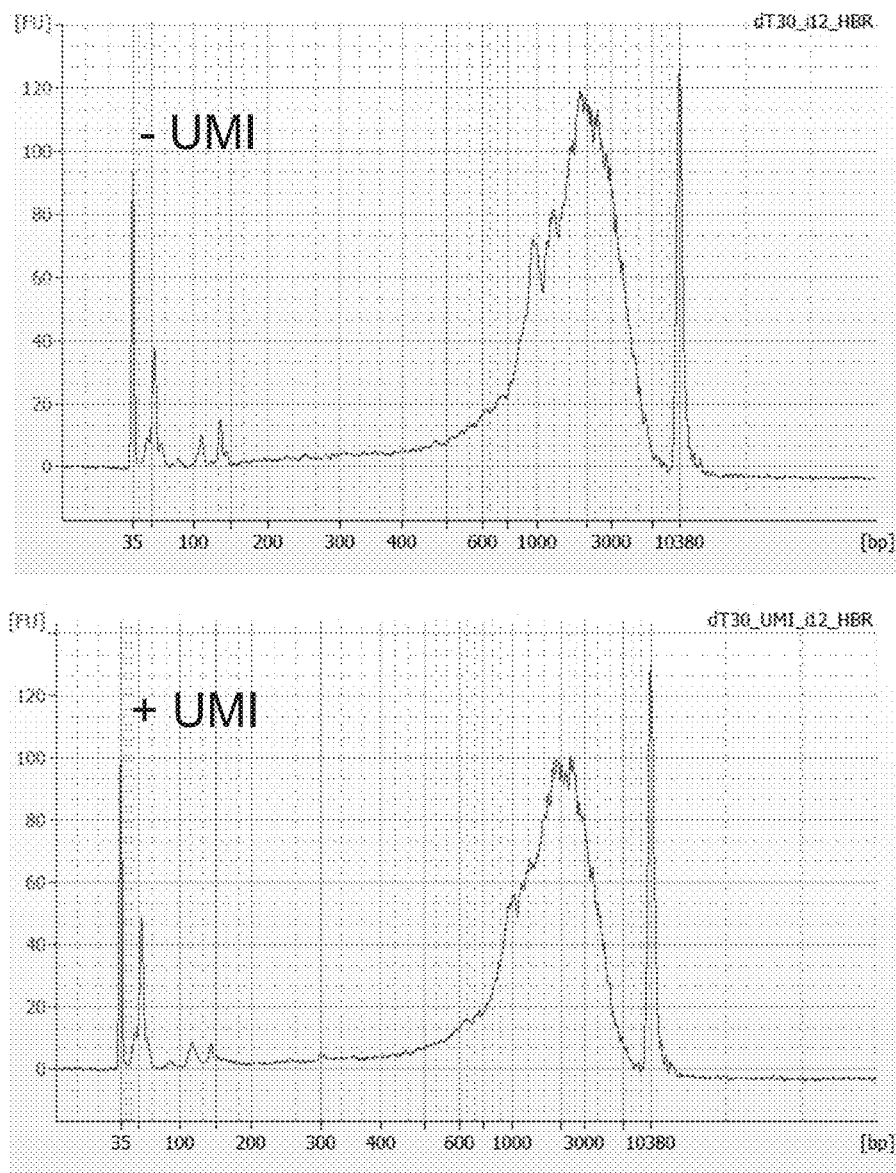
FIG. 11A provides graphical representations of the results from an experiment configured to determine the effect of a unique molecular identifier (UMI) on an Oligo dT primer, e.g., as illustrated in FIG. 11B.

In one embodiment, a molecular index (i.e., UMI) is present on the first strand cDNA synthesis primer. In this example, the UMI is a sequence of six random nucleotides (N, where N can be either A, T, G, or C). In the first strand cDNA synthesis primer it is present 5' of the oligodT stretch used for cDNA synthesis and 3' of the cell barcode. The CDS primer was synthesized as shown in FIG. 11B.

To investigate the effect of the UMI, four libraries were generated using the embodiment described in FIG. 3A, except two of the four cDNA synthesis oligo had a UMI sequence as described above. Two libraries were generated starting with 10 pg of Mouse Brain (MB) RNA (Clontech) both with barcode index 6. And two libraries were generated starting with 10 pg of Human Brain (HB) RNA (Clontech) with barcode index 12. One library derived from each RNA type had a UMI and one did not, for comparison. The two cDNAs synthesized with the HB RNA and the same index were visualized on a Bioanalyzer, and FIG. 11A and Table 1 indicate that both cDNA oligonucleotides were capable of producing full-length cDNA that was of expected yield and size distribution.

The two mouse brain (MB) derived cDNA was tagmented and amplified as described in FIG. 3A, and the resultant libraries were applied to MiSeq with read 1 of 57 cycles. STAR aligner was used for the mapping against the mouse genome. The results of mapping are in Table 2, and show that libraries made with or without the presence of the UMI have a high mapping percentage (95-96%), and identify a high number of genes (>10,000 at an expression level of >0.1 RPKM or >9,000 at an expression level of >1 RPKM). The percent of reads that are derived from the sense strand of the transcript is also high (99% for both libraries), a metric consistent with the library design. Finally, a Pearson analysis of the two libraries has a high correlation (0.97), indicating that the presence of the UMI did not change the content of the cDNA library dramatically.

TABLE 1 cDNA statistics

| | Size [bp] | Conc. [pg/μl] | Molarity [pmol/l] | Yield [ng] |
|---|---|---|---|---|
| −UMI | 1,859 | 922.7 | 751.8 | 11.1 |
| +UMI | 2,424 | 734.3 | 459 | 8.8 |

TABLE 2

Sequencing statistics

| UMI (N6) | − | + |
|---|---|---|
| Number of input reads | 1,254,480 | 1,582,136 |
| % of total mapped read | 96.40% | |
| Strandedness | 99% | 94.90% |
| RPKM > 0.1 | 10,306 | 99% |
| RPKM > 1 | 9,402 | 10,264 |
| Pearson correlation | 0.97 | 9,363 |

Notwithstanding the appended clauses, the disclosure is also defined by the following clauses:

1. A method of preparing a next generation sequencing (NGS) library from a ribonucleic acid (RNA) sample, the method comprising:
   (a) combining:
      a RNA sample;
      a first strand cDNA primer comprising a first pre-tagmentation amplification, e.g., polymerase chain reaction (PCR), primer binding domain;
      a template switch oligonucleotide comprising a 3' hybridization domain and a 5' second pre-tagmentation amplification, e.g., PCR, primer binding domain;
      a reverse transcriptase; and
      dNTPs;
   in a reaction mixture under conditions sufficient to produce a double stranded product nucleic acid comprising a template mRNA and the template switch oligonucleotide each hybridized to adjacent regions of a first strand complementary deoxyribonucleic acid (cDNA), wherein one of the first strand cDNA primer and the template switch oligonucleotide comprises a first post-tagmentation amplification, e.g., PCR, primer binding domain; and
   (b) contacting the product nucleic acid with first and second amplification, e.g., PCR, primers complementary to the first and second primer binding domains under amplification, e.g., PCR amplification, conditions sufficient to produce a product double stranded cDNA.

2. The method according to Clause 1, wherein the method further comprises tagmenting the product double stranded cDNA with a transposome comprising a transposase and a transposon nucleic acid comprising a transposon end domain and a second post-tagmentation amplification, e.g., PCR, primer binding domain to produce a tagmented sample.

3. The method according to Clause 3, wherein the method further comprises amplifying the tagmented sample by contacting the tagmented sample with:
   a first primer comprising a first post-tagmentation amplification, e.g., PCR amplification, primer domain, a first NGS indexing domain and a first NGS adapter domain; and
   a second primer comprising a second post-tagmentation amplification, e.g., PCR amplification, primer domain, a second NGS indexing domain and a second NGS adapter domain;
   under PCR amplification conditions sufficient to produce a NGS library.

4. The method according to any of Clauses 1 to 3, wherein the RNA sample comprises messenger RNA and the method comprises producing the NGS library from mRNA.

5. The method according to Clause 4, wherein the first strand cDNA primer comprises an oligodT domain 3' of the first pre-tagmentation amplification primer binding domain.

6. The method according to any of Clauses 1 to 5, wherein the first strand cDNA primer comprises the first post-tagmentation amplification primer binding domain.

7. The method according to any of Clauses 1 to 5, wherein the template switch oligonucleotide comprises the first post-tagmentation amplification primer binding domain.

8. The method according to any of the preceding clauses, wherein the first post-tagmentation amplification primer binding domain comprises an NGS read primer domain.

8. The method according to any of the preceding clauses, wherein the second post-tagmentation PCR primer binding domain comprises an NGS read primer domain.

9. The method according to any of the preceding clauses, wherein the first strand cDNA primer further comprises a source barcode domain.

10. The method according to any of the preceding clauses, wherein the first and second pre-tagmentation amplification primer binding domains are identical.

11. The method according to Clause 10, wherein the first and second pre-tagmentation amplification primers are identical.

12. The method according to any of the preceding clauses, wherein at least one of the first strand cDNA primer, template switch oligonucleotide and pre-tagmentation primers comprises a 5' polymerase blocking modification.

13. The method according to Clause 12, wherein each of the first strand cDNA primer and pre-tagmentation primers comprises a 5' polymerase blocking modification.

14. The method according to Clauses 12 and 13, wherein the 5' polymerase blocking modification is selected from the group consisting of: an abasic lesion, a nucleotide adduct, an iso-nucleotide base, and combinations thereof.

15. The method according to any of the preceding clauses, wherein at least one of the first strand cDNA primer, template switch oligonucleotide and pre-tagmentation amplification primers comprises one or more nucleotide analogs.

16. The method according to Clause 15, wherein each of the first strand cDNA primer, template switch oligonucleotide and pre-tagmentation amplification primers comprises one or more nucleotide analogs.

17. The method according to any the preceding clauses, wherein the 3' hybridization domain comprises a homo-nucleotide stretch.

18. The method according to any of Clauses 1 to 17, wherein the 3' hybridization domain comprises a hetero-nucleotide stretch.

19. The method according to any of the preceding clauses, wherein the transposase comprises a Tn5 transposase.

20. The method according to Clause 19, wherein the transposon end domain comprises a Tn5 transposon end domain.

21. The method according to any of Clauses 1 to 20, wherein the method further comprises pooling the double stranded product cDNA with a second double stranded product cDNA to produce a pooled cDNA sample, and then tagmenting the pooled cDNA sample.

22. The method according to any of the preceding clauses, wherein the RNA sample is one that is produced from a single cell.

23. The method according to any of the preceding clauses, wherein the method further comprises subjecting the NGS library to an NGS protocol.

24. The method according to any of the preceding clauses, wherein the method further comprises quantitating one or more RNA species of the RNA sample.

25. A composition comprising a template mRNA and a template switch oligonucleotide each hybridized to adjacent regions of a first strand cDNA, wherein one of the first strand cDNA and the template switch oligonucleotide comprises first post-tagmentation amplification, e.g., PCR, primer binding domain.

26. The composition according to Claim 25, wherein the first strand cDNA comprises the first post-tagmentation amplification primer binding domain.

27. The composition according to Claim 25, wherein the template switch oligonucleotide comprises the first post-tagmentation amplification primer binding domain.

28. The composition according to any of Clauses 25 to 27, wherein the first strand cDNA further comprises a source barcode domain.

29. A composition comprising a double stranded cDNA produced from the composition according to any of Clauses 25 to 28.

30. A composition comprising a tagmented sample produced by tagmenting a double stranded cDNA according to Clause 29 with a transposome comprising a transposase and a transposon nucleic acid comprising a transposon end domain and a second post-tagmentation amplification, e.g., PCR, primer binding domain to produce a tagmented sample.

31. A NGS library produced by amplification of a tagmented sample according to Clause 30, wherein the NGS library comprises a plurality of doubled stranded NGS ready deoxyribonucleic acids (DNAs) that each comprises terminal sequencing platform adapter constructs.

32. The composition according to Clause 31, wherein the sequencing platform adapter constructs comprise adaptor and indexing sequences.

33. A kit comprising:
a first strand cDNA primer comprising an 3' RNA hybridization domain and a 5' first pre-tagmentation amplification, e.g., PCR amplification, primer binding domain; and
a template switch oligonucleotide comprising a 3' hybridization domain and a 5' second pre-tagmentation amplification, e.g., PCR amplification, primer binding domain;
wherein one of the first strand cDNA primer and template switch oligonucleotide further comprises a first post-tagmentation amplification, e.g., PCR amplification, primer binding domain.

34. The kit according to Clause 33, wherein the first strand cDNA primer comprises the first post-tagmentation amplification primer binding domain.

35. The kit according to Clause 33, wherein the template switch oligonucleotide comprises the first post-tagmentation amplification primer binding domain 36. The kit according to any of Clauses 33 to 35, wherein the first and second pre-tagmentation amplification, e.g., PCR amplification, primer binding domains are identical.

37. The kit according to any of Clauses 33 to 36, wherein the kit further comprises first and second pre-tagmentation amplification, e.g., PCR amplification, primers.

38. The kit according to Clause 37, wherein the first and second pre-tagmentation amplification primers are identical.

39. The kit according to any of Clauses 33 to 38, wherein the kit further comprises a transposome comprising a transposase and a transposon nucleic acid comprising a transposon end domain and a second post-tagmentation amplification, e.g., PCR amplification, primer binding domain.

40. The kit according to Clause 39, wherein the transposase comprises a Tn5 transposase.

41. The kit according to Clauses 39 or 40, wherein the transposon end domain comprises a Tn5 transposon end domain.

42. The kit according to Clauses 39 to 41, wherein the kit further comprises:
a first primer comprising a first post-tagmentation amplification, e.g., PCR amplification, primer binding domain, a first NGS indexing domain and a first NGS adapter domain; and
a second primer comprising a second post-tagmentation amplification, e.g., PCR amplification, primer binding domain, a second NGS indexing domain and a second NGS adapter domain.

43. The kit according to any of Clauses 33 to 42, wherein the kit further comprises a solid support.

44. The kit according to any of Clauses 33 to 43, wherein the kit comprises a lyophilized component.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of preparing a next generation sequencing (NGS) library from a ribonucleic acid (RNA) sample, the method comprising:
(a) combining:
   a RNA sample;
   a first strand complementary deoxyribonucleic acid (cDNA) primer comprising a first pre-tagmentation amplification primer binding domain;
   a template switch oligonucleotide comprising a 3' hybridization domain and a 5' second pre-tagmentation amplification primer binding domain;
   a reverse transcriptase; and
   dNTPs;
   in a reaction mixture under conditions sufficient to produce a double stranded product nucleic acid comprising a template mRNA and the template switch oligonucleotide each hybridized to adjacent regions of a first strand cDNA, wherein only one of the first strand cDNA primer and the template switch oligonucleotide comprises a first post-tagmentation amplification primer binding domain; and
(b) contacting the product nucleic acid with first and second pre-tagmentation amplification primers complementary to the first and second pre-tagmentation amplification primer binding domains under amplification conditions sufficient to produce a product double stranded cDNA;
(c) tagmenting the product double stranded cDNA with a transposome comprising a transposase and a transposon nucleic acid comprising a transposon end domain and a second post-tagmentation amplification primer binding domain to produce a tagmented sample; and
(d) amplifying the tagmented sample by contacting the tagmented sample with:
   a first post-tagmentation primer comprising a first post-tagmentation amplification primer domain complementary to the first post-tagmentation amplification primer binding domain; and
   a second primer comprising a second post-tagmentation amplification primer domain complementary to the second post-tagmentation amplification primer binding domain.

2. The method according to claim 1, wherein
the first post-tagmentation primer further comprises a first NGS indexing domain and a first NGS adapter domain; and
the second post-tagmentation primer further comprises a second NGS indexing domain and a second NGS adapter domain.

3. The method according to claim 1, wherein the RNA sample comprises messenger RNA and the method comprises producing the NGS library from mRNA.

4. The method according to claim 1, wherein the first strand cDNA primer comprises the first post-tagmentation amplification primer binding domain.

5. The method according to claim 1, wherein the template switch oligonucleotide comprises the first post-tagmentation amplification primer binding domain.

6. The method according to claim 1, wherein the first and second pre-tagmentation amplification primer binding domains are identical and the first and second pre-tagmentation amplification primers are identical.

7. The method according to claim 1, wherein the transposase comprises a Tn5 transposase.

8. The method according to claim 7, wherein the transposon end domain comprises a Tn5 transposon end domain.

9. The method according to claim 1, wherein the method further comprises pooling the double stranded product cDNA with a second double stranded product cDNA to produce a pooled cDNA sample, and then tagmenting the pooled cDNA sample.

10. The method according to claim 1, wherein the RNA sample is one that is produced from a single cell.

11. The method according to claim 1, wherein the method further comprises subjecting the NGS library to an NGS protocol.

12. The method according to claim 1, wherein the method further comprises quantitating one or more RNA species of the RNA sample.

13. The method according to claim 4, wherein the first strand cDNA primer comprises an oligodT domain 3' of the first pre-tagmentation amplification primer binding domain.

14. The method according to claim 1, wherein the first strand cDNA primer further comprises a source barcode domain.

15. The method according to claim 1, wherein at least one of the first strand cDNA primer, template switch oligonucleotide and pre-tagmentation amplification primers comprises one or more nucleotide analogs.

16. The method according to claim 15, wherein each of the first strand cDNA primer, template switch oligonucleotide and pre-tagmentation amplification primers comprises one or more nucleotide analogs.

17. The method according to claim 15, wherein the one or more nucleotide analogs is selected from the group consisting of: an abasic lesion, a nucleotide adduct, an iso-nucleotide base, linkage modifications, 5' and/or 3' end modifications, one or more fluorescently labeled nucleotides, and combinations thereof.

18. The method according to claim 17, wherein the one or more nucleotide analogs comprises a 5' end modification.

19. The method according to claim 1, wherein at least one of the first strand cDNA primer, template switch oligonucleotide and pre-tagmentation primers comprises a 5' polymerase blocking modification.

20. The method according to claim 19, wherein each of the first strand cDNA primer and pre-tagmentation primers comprises a 5' polymerase blocking modification.

21. The method according to claim 19, wherein the 5' polymerase blocking modification is selected from the group consisting of: an abasic lesion, a nucleotide adduct, an iso-nucleotide base, and combinations thereof.

22. The method according to claim 1, wherein the 3' hybridization domain comprises a homonucleotide stretch.

23. The method according to claim 1, wherein the 3' hybridization domain comprises a heteronucleotide stretch.

* * * * *

UNITED STATES PATENT AND TRADEMARK OFFICE
CERTIFICATE OF CORRECTION

PATENT NO. : 10,870,848 B2
APPLICATION NO. : 15/746781
DATED : December 22, 2020
INVENTOR(S) : Cynthia Chang et al.

Page 1 of 1

It is certified that error appears in the above-identified patent and that said Letters Patent is hereby corrected as shown below:

In the Specification

Please replace "weds" with -- wells -- (Column 24, Line 45).

Signed and Sealed this
Twenty-fourth Day of August, 2021

Drew Hirshfeld
*Performing the Functions and Duties of the
Under Secretary of Commerce for Intellectual Property and
Director of the United States Patent and Trademark Office*

SEQUENCE LISTING

<160> NUMBER OF SEQ ID NOS: 8

<210> SEQ ID NO 1
<211> LENGTH: 20
<212> TYPE: DNA
<213> ORGANISM: Artificial sequence
<220> FEATURE:
<223> OTHER INFORMATION: synthetic sequence

<400> SEQUENCE: 1
aatgatacgg cgaccaccga                                         20

```
<210> SEQ ID NO 2
<211> LENGTH: 24
<212> TYPE: DNA
<213> ORGANISM: Artificial sequence
<220> FEATURE:
<223> OTHER INFORMATION: synthetic sequence

<400> SEQUENCE: 2
caagcagaag acggcatacg agat                                              24

<210> SEQ ID NO 3
<211> LENGTH: 33
<212> TYPE: DNA
<213> ORGANISM: Artificial sequence
<220> FEATURE:
<223> OTHER INFORMATION: synthetic sequence

<400> SEQUENCE: 3
acactctttc cctacacgac gctcttccga tct                                    33

<210> SEQ ID NO 4
<211> LENGTH: 34
<212> TYPE: DNA
<213> ORGANISM: Artificial sequence
<220> FEATURE:
<223> OTHER INFORMATION: synthetic sequence

<400> SEQUENCE: 4
gtgactggag ttcagacgtg tgctcttccg atct                                   34

<210> SEQ ID NO 5
<211> LENGTH: 30
<212> TYPE: DNA
<213> ORGANISM: Artificial sequence
<220> FEATURE:
<223> OTHER INFORMATION: synthetic sequence

<400> SEQUENCE: 5
ccatctcatc cctgcgtgtc tccgactcag                                        30

<210> SEQ ID NO 6
<211> LENGTH: 23
<212> TYPE: DNA
<213> ORGANISM: Artificial sequence
<220> FEATURE:
<223> OTHER INFORMATION: synthetic sequence

<400> SEQUENCE: 6
cctctctatg ggcagtcggt gat                                               23

<210> SEQ ID NO 7
<211> LENGTH: 19
<212> TYPE: DNA
<213> ORGANISM: Artificial sequence
<220> FEATURE:
<223> OTHER INFORMATION: synthetic sequence

<400> SEQUENCE: 7
agatgtgtat aagagacag                                                    19

<210> SEQ ID NO 8
<211> LENGTH: 19
<212> TYPE: DNA
<213> ORGANISM: Artificial sequence
<220> FEATURE:
<223> OTHER INFORMATION: synthetic sequence
```

```
<400> SEQUENCE: 8
ctgtctctta tacacatct                                                    19
```